(12) United States Patent
Hiddessen et al.

(10) Patent No.: US 9,328,376 B2
(45) Date of Patent: May 3, 2016

(54) SYSTEMS AND METHODS FOR STABILIZING DROPLETS

(71) Applicant: BIO-RAD LABORATORIES, INC., Hercules, CA (US)

(72) Inventors: Amy L. Hiddessen, Tracy, CA (US); Erin R. Chia, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/018,205

(22) Filed: Sep. 4, 2013

(65) Prior Publication Data

US 2014/0170665 A1    Jun. 19, 2014

Related U.S. Application Data

(60) Provisional application No. 61/697,232, filed on Sep. 5, 2012.

(51) Int. Cl.
| | |
|---|---|
| *C12Q 1/68* | (2006.01) |
| *B01L 3/00* | (2006.01) |
| *B01L 7/00* | (2006.01) |

(52) U.S. Cl.
CPC ......... *C12Q 1/6806* (2013.01); *B01L 3/502784* (2013.01); *B01L 7/525* (2013.01); *B01L 2200/0673* (2013.01); *B01L 2300/0816* (2013.01); *B01L 2300/0867* (2013.01); *B01L 2300/1822* (2013.01); *B01L 2300/1827* (2013.01); *B01L 2400/0487* (2013.01)

(58) Field of Classification Search
CPC ................... B01L 2200/0673; B01L 3/502784
See application file for complete search history.

(56) References Cited

U.S. PATENT DOCUMENTS

| | | | |
|---|---|---|---|
| 2005/0172476 A1* | 8/2005 | Stone et al. | 29/592.1 |
| 2006/0257893 A1* | 11/2006 | Takahashi et al. | 435/6 |
| 2007/0054119 A1* | 3/2007 | Garstecki et al. | 428/402 |
| 2009/0181864 A1* | 7/2009 | Nguyen et al. | 506/33 |
| 2010/0173394 A1 | 7/2010 | Colston, Jr. et al. | |
| 2010/0187705 A1 | 7/2010 | Lee et al. | |
| 2011/0129941 A1 | 6/2011 | Kumacheva et al. | |
| 2011/0217712 A1 | 9/2011 | Hiddessen et al. | |
| 2012/0208241 A1 | 8/2012 | Link | |

OTHER PUBLICATIONS

International search report and written opinion dated Dec. 12, 2013 for PCT/US2013/058103.

* cited by examiner

*Primary Examiner* — Paul Hyun
(74) *Attorney, Agent, or Firm* — Kolisch Hartwell, P.C.

(57) ABSTRACT

This disclosure provides systems, devices, and methods for sample preparation and/or analysis comprising a droplet generator having a first channel in fluid communication with a carrier fluid reservoir and a second channel in fluid communication with a sample reservoir. The first channel and second channel may meet at an intersection that receives a sample from the sample reservoir and a carrier fluid from the carrier fluid reservoir and generates one or more droplets that flow along a droplet channel to a droplet reservoir. An energy application member in thermal communication with the intersection, at least a portion of the droplet channel, the sample reservoir and/or the carrier fluid reservoir may provide energy to an individual droplet of the one or more droplets, such as at the intersection and/or as the droplet moves along the droplet channel to the droplet reservoir.

13 Claims, 11 Drawing Sheets

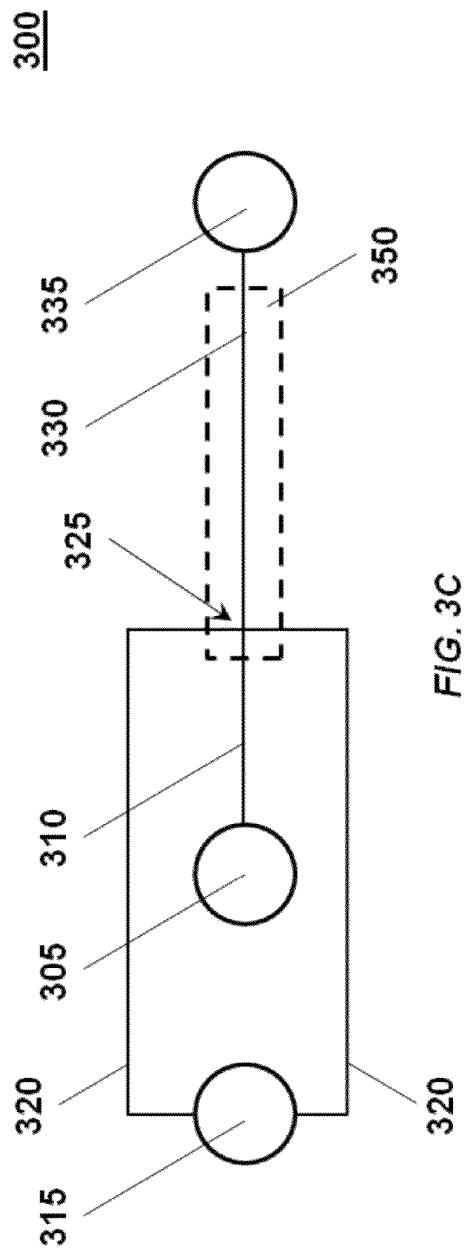
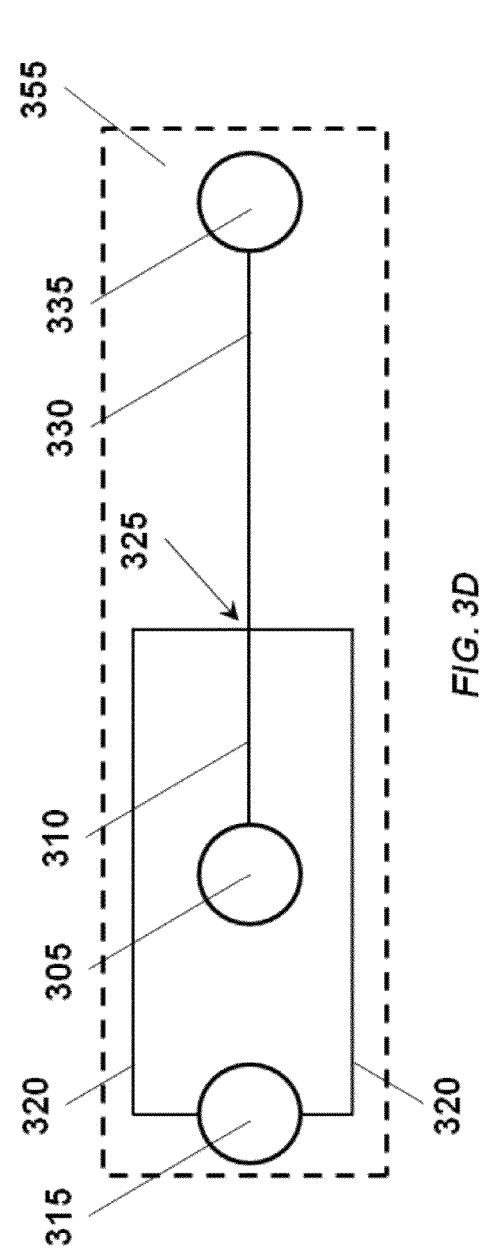

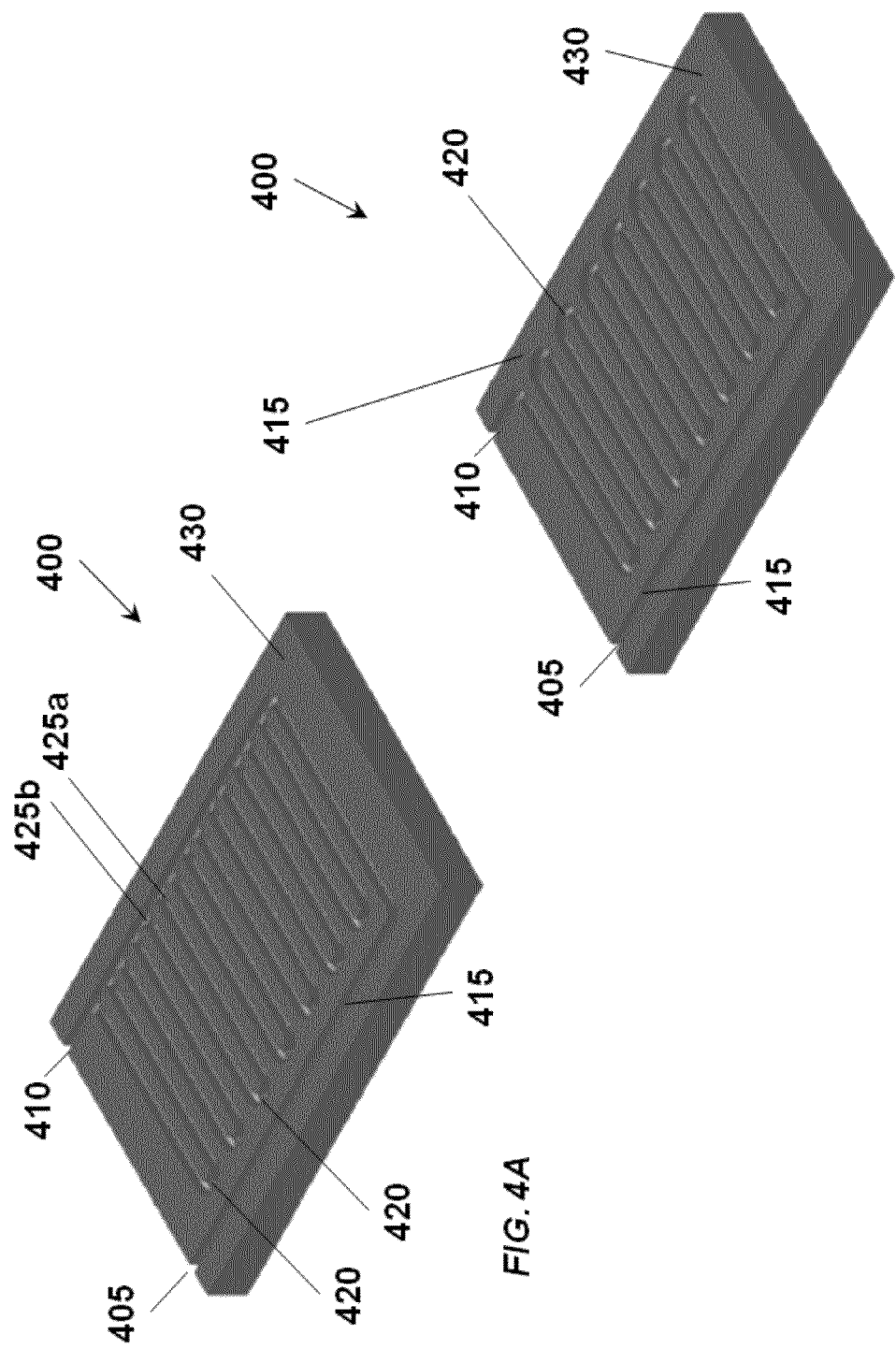

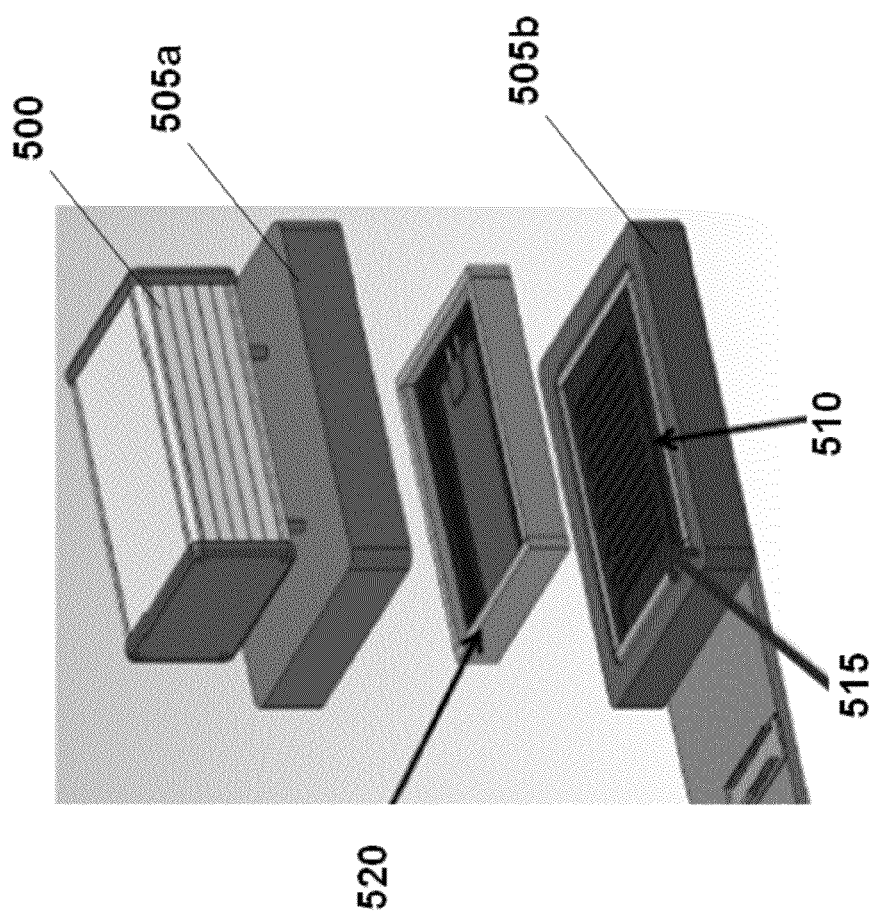

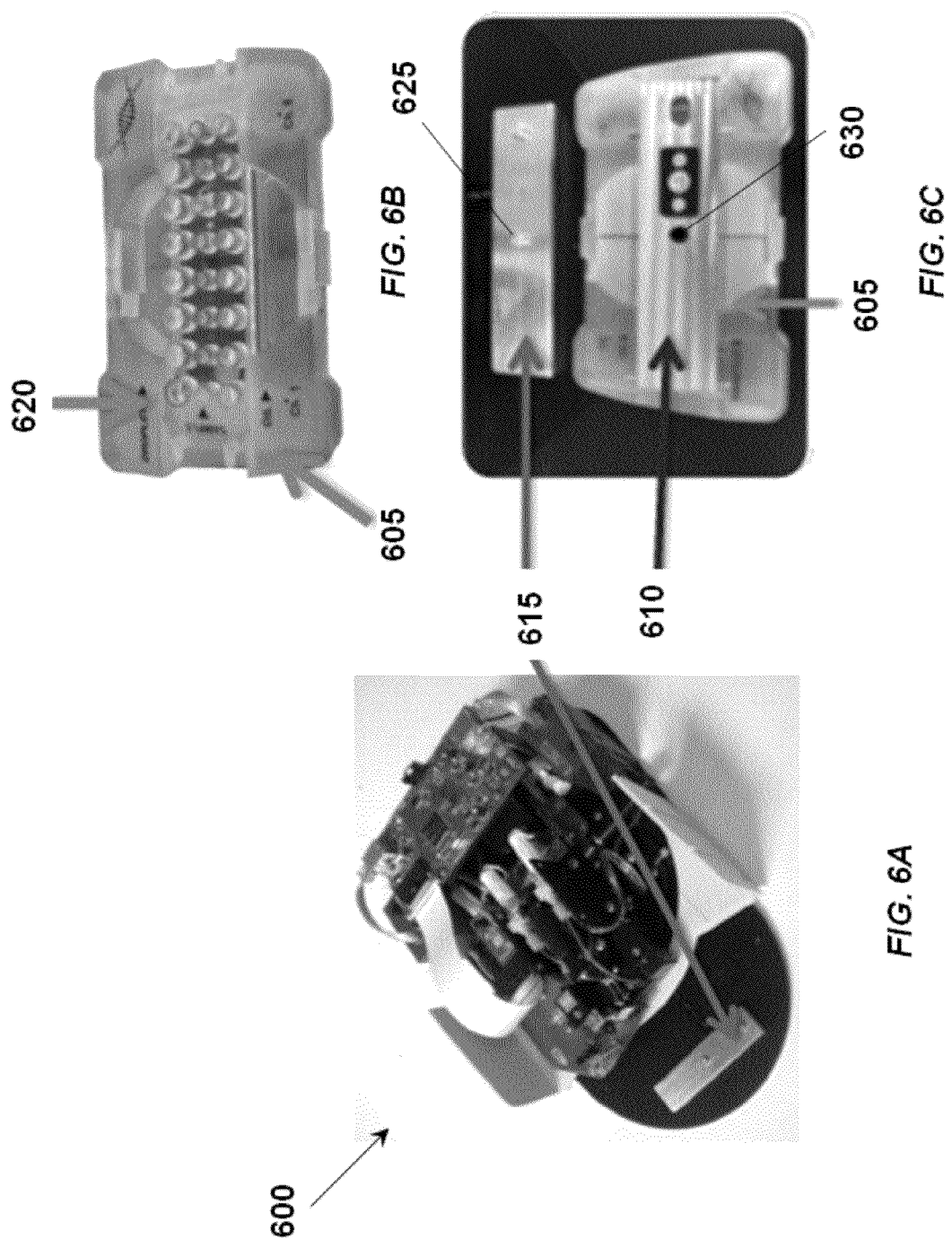

SYSTEMS AND METHODS FOR STABILIZING DROPLETS

CROSS-REFERENCE

This application claims priority to U.S. Provisional Patent Application No. 61/697,232, filed Sep. 5, 2012, which is entirely incorporated herein by reference.

BACKGROUND

Assays are generally procedures for determining the presence, quantity, activity, and/or other properties or characteristics of components in a sample. In some cases, the samples to be assayed are complex, the components of interest within the samples—e.g., a nucleic acid, an enzyme, a virus, a bacterium—are only minor constituents of the samples, and the results of the assays are required quickly and/or for many samples.

Some current systems perform assays with the aid of droplets generated in drop generators. Often, the droplet generators work by partitioning a sample into multiple droplets. The sample may be an aqueous sample that is contacted with a stream of oil fluid in such a way as to form a disperse phase of aqueous droplets in a continuous oil phase. In such systems, droplets with sample partitions are generated for storage in a droplet storage vessel, which sample can subsequently be processed (e.g., amplified in the case of PCR) and analyzed.

Due to the sensitivity of droplets to mechanical motion and accompanying shear forces, care is ordinarily taken in transporting droplets to a droplet storage vessel, or directing a droplet from the droplet generator to a processing station and subsequently a droplet reader. Improved droplet generation mechanisms would be of great benefit to biological and clinical assays that use droplet-based assays.

SUMMARY

Droplet damage can reduce droplet data quality in systems that may depend on droplet integrity, such as droplet-based digital polymerase chain reaction (PCR) systems. Droplets may be susceptible to damage (e.g., coalescence, break-up) during operations on droplets, such as, for example, pipette transfer of pre-PCR droplets from one vial to another. In some cases this is due to mechanical forces, such as shear forces, as may be provided upon pipetting droplets through an orifice and into the barrel of the pipette tip at varying speeds and/or with varying amounts of volume ratios of droplets and air; pressure changes; introduction to air or other fluids; and exposure to plastic surfaces (such as dry plastic surfaces that are highly charged and can cause electro-coalescence).

In view of at least the limitations of current droplet generators, recognized herein is the need for improved systems and methods for forming droplets. In particular, recognized herein is the need for droplet generators and systems for forming droplets that are more stable, thereby enabling a decrease in processing time.

Some embodiments provide an on-board system for droplet generation that induces droplet stabilization in order to reduce droplet damage upon transfer from a droplet generator apparatus and/or consumable to a receiving system, such as a receiving vial, plate, fluidics station or other system downstream of the droplet generator, such as a droplet detector.

The present disclosure applies to any optical, mechanical, electrical or chemical induction of droplet stabilization that physically or chemically alters the droplet properties to make them stronger and thereby more resistant to processing and/or analysis steps downstream of the point of droplet generation, which includes, but is not limited to, pipetting, droplet transfer steps, additional thermal and/or other chemical stresses, and fluidic manipulation.

In some embodiments, droplet stabilization is achieved using or with the aid of a skin (or shell) formed around the droplet, which can be implemented with the aid of hardware on the droplet generator. The hardware can include a heating system in thermal communication with various points along a fluid flow path comprising the droplet generator. The skin is formed at an interface between the droplet and a carrier fluid having the droplet, such as oil.

Systems and methods provided herein are readily applicable to droplet chemistries which have heat-induced stabilization mechanisms, such as a skin. The skin can be formed upon the application of heat to the droplet.

Systems and methods provided herein may be used for a variety of applications, such as, for example, activation, deactivation or destruction of temperature-sensitive enzymes; modulation of temperature to avoid shifts in temperature that can affect sensitive reagents (e.g., enzymes, dyes).

The present disclosure includes an on-board heating mechanism to stabilize droplets prior to a user transferring the droplet to another system for sample processing and/or analysis, such as a receiving vial/plate (e.g., PCR plate). In some cases, heat can be added to a fluid flow path of a droplet generator to thermally incubate droplets during and/or after droplet generation. In an example, heat is added to the interface plate below the consumable chip. The region can be limited, for example, to the row of wells in the chip that contain droplets. In some cases, the entire consumable is heated.

In some embodiments, a fluid flow path of a droplet generator is under thermal control. In other embodiments, the droplet generator and/or consumable are under thermal control.

In some embodiments, droplet stability, such as skin formation, is facilitated with the aid of heat activated cross-linking during and/or subsequent to droplet generation. Droplets can be heated in microfluidic channels, which in turn can depend on the droplet residence time in the channels. In some cases, droplets are heated in-line right after they leave the generation site. Such heating can be coupled with fluid mixing, such as mixing at an intersection of a plurality of droplet generators, and/or mixing along a fluid flow path, such as a curvilinear (e.g., serpentine) fluid flow path.

In some embodiments, droplet stability, such as skin formation, is facilitated with the aid of photo or optically activated cross-linking during and/or subsequent to droplet generation. Droplet chemistry can include a chemically inducible component that is susceptible to cross-linking at an interface of the droplet, such as at an interface between a first phase of the droplet and a second phase of a fluid having the droplet. Cross-linking can be induced upon the application of electromagnetic radiation to such a droplet, such as with the aid of ultraviolet (UV), infrared (IR), or visible light. In some cases, cross-linking can be induced upon the application of energy with the aid of a laser.

Systems and methods provided herein enable improved consistency in droplet quality across experimental setups, droplet generators and/or droplet detectors. In some cases, systems provided herein enable reduced variability among droplet generators—a droplet formed in one system can be qualitatively similar to a droplet formed in another system. The present disclosure provides for a system having a low coefficient of variation (CV), such as less than 20%, 15%, 10%, 5%, 4%, 3%, 2%, 1%, 0.1%, or less.

In an aspect, a method of sample preparation comprises providing a microfluidic device comprising a droplet generator, a sample well, an oil well, and a droplet well, wherein the droplet generator is in fluid communication with the sample well, the oil well and the droplet well. Next, an aqueous sample fluid is loaded into the sample well and an immiscible oil is loaded into the oil well. The oil well and sample well are in fluid communication with a downstream intersection that generates droplets from a sample or sample partition and the immiscible oil.

During operation, the pressure in the droplet well can be adjusted to be lower than the pressures in the sample well and the pressure in the oil well. The pressure difference can cause the aqueous sample fluid to flow toward the droplet generator and causes the immiscible oil to flow toward the intersection. At the intersection, the flow of the aqueous sample fluid and the immiscible oil are capable of partitioning the aqueous sample fluid into droplets. Droplets flow along a droplet channel to a droplet well (or reservoir), where droplets are collected. One or more of the aqueous sample, the immiscible oil and the droplets are heated to provide stabilized droplets. Stabilized droplets can be removed from the droplet well.

In another aspect, a system for sample preparation and/or analysis comprises a droplet generator comprising a first channel in fluid communication with a carrier fluid reservoir and a second channel in fluid communication with a sample reservoir, the first channel and second channel meeting at an intersection that receives a sample from the sample reservoir and a carrier fluid from the carrier fluid reservoir and generates one or more droplets that flow along a droplet channel to a droplet reservoir; and an energy application member in thermal communication with (i) the intersection, (ii) at least a portion of the droplet channel, (iii) the carrier fluid reservoir and/or (iv) the sample reservoir. The energy application member can transfer energy to an individual droplet of the one or more droplets at the intersection, the carrier fluid reservoir and/or the sample reservoir. In an embodiment, transferring energy to an individual droplet of the one or more droplets forms a skin around the individual droplet. In another embodiment, the skin has an area compressibility modulus between about 0.01 mN/m to 10000 mN/m at a temperature of about 25° C. In another embodiment, the system further comprises a third channel in fluid communication with the carrier fluid reservoir, the third channel meeting with the first and second channels at the intersection. In another embodiment, the one or more droplets flow along the droplet channel as an emulsion. In another embodiment, the energy application member comprises one or more resistive heating element. In another embodiment, the energy application member comprises a thermoelectric device thermally coupled to the droplet channel. In another embodiment, the droplet generator is included in a housing having a plurality of droplet generators.

In an embodiment, the system further comprises a pressure source for facilitating the flow of the individual droplet to the droplet reservoir. In another embodiment, the pressure source includes a source of positive pressure. In another embodiment, the energy application member is a heating member. In another embodiment, the energy application member transfers thermal energy to an individual droplet of the one or more droplets at the intersection, the carrier fluid reservoir and/or the sample reservoir. In another embodiment, transferring energy to an individual droplet of the one or more droplets stabilizes the individual droplet. In another embodiment, the energy application member comprises a plurality of energy application elements. In another embodiment, the energy application member thermally cycles the one or more droplets to induce nucleic acid amplification in the one or more droplets. In another embodiment, the energy application member provides energy in the form of an energy gradient. In another embodiment, the individual droplet includes a sample partition. In another embodiment, the sample partition is prepared as a reaction mixture for amplification of a nucleic acid target. In another embodiment, the energy application member comprises an interface plate that is formed of a metallic material. In another embodiment, the energy application member is integrated with the droplet generator. In another embodiment, the energy application member is removable from the droplet generator. In another embodiment, the system further comprises a detection assembly between the intersection and the droplet reservoir, the detection assembly for detecting signals from the one or more droplets. In another embodiment, the energy application member provides thermal energy, electromagnetic energy, electrical energy, chemical energy, or mechanical energy, or any combination thereof. In another embodiment, the electromagnetic energy is gamma rays, x-rays, ultraviolet rays, visible light, infrared rays, microwaves, radio waves, or any combination thereof. In another embodiment, the thermal energy is heat, conduction, convection, radiation, or a combination thereof.

In an embodiment, the energy application member provides energy with the aid of one or more heating elements. In another embodiment, the one or more heating elements comprise a resistive heating element, thermoelectric device, heating block, lamp, light source, microwave, radiation source, water bath, or any combination thereof. In another embodiment, the one or more heating elements comprise a first heating element and a second heating element. The first heating element can provide a first energy and the second heating element can provide a second energy. In another embodiment, the first energy provides droplet stabilization and the second energy initiates and/or facilitates a reaction within an individual droplet. In another embodiment, the reaction comprises PCR, reverse transcription polymerase chain reaction (RT-PCR), isothermal amplification, in vitro translation, or a combination thereof.

In an embodiment, the energy application member is in thermal communication with any two of (i)-(iv). In another embodiment, the energy application member is in thermal communication with any three of (i)-(iv). In another embodiment, the energy application member is in thermal communication with each of (i)-(iv).

In another aspect, a method for generating a droplet comprises forming one or more droplets using any of the systems above or elsewhere herein, alone or in combination.

In another aspect, a method for forming a droplet containing a sample to be detected comprises (a) generating a droplet at an intersection of a first channel and a second channel, the first channel in fluid communication with a carrier fluid reservoir and the second channel in fluid communication with a sample reservoir, wherein the droplet is generated by bringing a carrier fluid from the carrier fluid reservoir in contact with a sample or sample partition from the sample reservoir at the intersection; (b) flowing the droplet along a droplet channel leading from the intersection to a droplet reservoir; and (c) providing thermal energy to the droplet at the intersection, the carrier fluid reservoir and/or the sample reservoir.

In an embodiment, providing thermal energy to the droplet comprises heating the droplet. In another embodiment, providing thermal energy to the droplet forms a skin around the droplet. In another embodiment, thermal energy is provided to the droplet with the aid of an energy application member coupled to the (i) intersection, (ii) at least a portion of the droplet channel, (iii) the carrier fluid reservoir and/or (iv) the sample reservoir. In another embodiment, the energy application member is coupled to any two of (i)-(iv). In another embodiment, the energy application member is coupled to any three of (i)-(iv). In another embodiment, the energy application member is coupled to each of (i)-(iv). In another embodiment, the energy application member transfers energy to the droplet as the droplet moves along the droplet channel to the droplet reservoir. In another embodiment, the energy application member comprises one or more resistive heating elements. In another embodiment, the energy application member comprises one or more thermoelectric devices thermally coupled to the droplet channel.

In an embodiment, the droplet flows along the droplet channel as an emulsion. In another embodiment, the droplet flows along the droplet channel with the aid of a pressure source. In another embodiment, the pressure source includes a source of positive pressure.

In an embodiment, the method further comprises thermally cycling the droplet to induce nucleic acid amplification. In another embodiment, the sample partition is prepared as a reaction mixture for amplification of a nucleic acid target. In another embodiment, the droplet is heated along a temperature gradient. In another embodiment, providing energy to the droplet comprises heating the droplet at the intersection. In another embodiment, the droplet is heated at the intersection by heating the carrier fluid prior to forming the droplet.

In an embodiment, providing thermal energy to the droplet comprises heating the droplet in the droplet channel. In another embodiment, the energy is thermal energy, electromagnetic energy, electrical energy, chemical energy, mechanical energy, or any combination thereof. In another embodiment, the electromagnetic energy is gamma rays, x-rays, ultraviolet rays, visible light, infrared rays, microwaves, radio waves, or any combination thereof. In another embodiment, the energy is thermal energy, and the thermal energy can be provided via energy transfer by conduction, convection, radiation, or any combination thereof. In another embodiment, the energy is thermal energy, and the thermal energy can be provided by one or more heating elements. In another embodiment, the one or more heating elements comprises a resistive heating element, thermoelectric device, heating block, lamp, light source, microwave, radiation source, water bath, or any combination thereof. In another embodiment, the one or more heating elements comprise a first heating element and a second heating element, and the first heating element provides a first energy and the second heating element provides a second energy. In another embodiment, the first and second energies allow for temperature cycling. In another embodiment, the first energy provides for droplet stabilization and the second energy initiates or facilitates a reaction within an individual droplet. In another embodiment, the reaction comprises PCR, RT-PCR, isothermal amplification, in vitro translation, or a combination thereof.

In an embodiment, providing thermal energy to the droplet stabilizes the droplet. In another embodiment, providing thermal energy to the droplet prevents the droplet from coalescing with another droplet.

In another aspect, method for forming droplets containing one or more samples or sample partitions comprises (a) generating droplets at an intersection of a first channel and a second channel, the first channel in fluid communication with a carrier fluid reservoir and the second channel in fluid communication with a sample reservoir, wherein the droplets are generated by bringing a carrier fluid from the carrier fluid reservoir in contact with a sample or sample partition from the sample reservoir at the intersection; (b) sequentially directing the droplets along a droplet channel leading from the intersection to a droplet reservoir; and (c) heating the droplets at the intersection, the carrier fluid reservoir and/or the sample reservoir.

In an embodiment, heating the droplets stabilizes the droplets. In another embodiment, heating the droplets prevents two or more of the droplets from coalescing together. In another embodiment, heating the droplets prevents 10% or more of a population of 20 or more droplets from coalescing. In another embodiment, the droplets flow along the droplet channel at a flow rate from about 0.5 microliter/minute to 10,000 microliters/minute. In another embodiment, the droplets flow along the droplet channel at a flow rate from about 1 microliter/minute to 5,000 microliters/minute. In another embodiment, energy is provided to the droplets under flow. In another embodiment, the droplets flow at a Weber number of 1 or less. In another embodiment, the droplets flow at a Reynolds number that is less than 2100. In another embodiment, the droplets flow at a Reynolds number that is greater than 2100. In another embodiment, the droplets flow at a Reynolds number that is between 0.1 and 1000.

In another aspect, a method for forming a droplet containing a sample or sample partition comprises (a) generating a droplet at an intersection of a first channel and a second channel, the first channel in fluid communication with a carrier fluid reservoir and the second channel in fluid communication with a sample reservoir, wherein the droplet is generated by bringing a carrier fluid from the carrier fluid reservoir in contact with a sample partition from the sample reservoir at the intersection; (b) flowing the droplet along a droplet channel leading from the intersection to a droplet reservoir; and (c) forming a skin around the droplet at or downstream of the intersection. In an embodiment, the method further comprises forming the skin by heating the droplet. In another embodiment, the skin is formed around the droplet at the intersection. In another embodiment, the skin is formed around the droplet in the droplet channel. In another embodiment, the method further comprises forming the skin by providing energy to the droplet. In another embodiment, the energy is thermal energy, electromagnetic energy, electrical energy, chemical energy, mechanical energy, or any combination thereof. In another embodiment, the electromagnetic energy is gamma rays, x-rays, ultraviolet rays, visible light, infrared rays, microwaves, radio waves, or any combination thereof. In another embodiment, the energy is thermal energy, and the thermal energy is transferred by conduction, convection, radiation, or any combination thereof. In another embodiment, the energy is thermal energy that is provided by one or more heating elements. In another embodiment, the one or more heating elements comprise a first heating element and a second heating element, and the first heating element provides a first energy and the second heating element provides a second energy. In another embodiment, the first and second energies allow for temperature cycling. In another embodiment, the first energy provides for droplet stabilization and the second energy initiates or facilitates a reaction within an individual droplet. In another embodiment, the reaction comprises PCR, RT-PCR, isothermal amplification, in vitro translation, or a combination thereof.

In an embodiment, forming the skin around the droplet stabilizes the droplet. In another embodiment, forming the skin around the droplet prevents the droplet from coalescing with another droplet. In another embodiment, the droplet flows along the droplet channel at a flow rate from about 0.5 microliter/minute to 10,000 microliters/minute. In another embodiment, the droplet flows along the droplet channel at a flow rate from about 1 microliter/minute to 5,000 microliters/minute. In another embodiment, the skin is formed around the droplet under flow. In another embodiment, the droplet flows along the droplet channel at a Weber number of 1 or less. In another embodiment, the droplet flows along the droplet channel at a Reynolds number less than 2100. In another embodiment, the droplet flows along the droplet channel at a Reynolds number greater than 2100. In another embodiment, the droplet flows along the droplet channel at a Reynolds number between 0.1 and 1000.

In another aspect, a system for sample preparation and/or analysis comprises a droplet generator having a first channel in fluid communication with a carrier fluid reservoir and a second channel in fluid communication with a sample reservoir, the first channel and second channel meeting at an intersection that receives a sample from the sample reservoir and a carrier fluid from the carrier fluid reservoir and generates one or more droplets that flow along a droplet channel to a droplet reservoir; and an energy application device coupled to (i) the intersection, (ii) at least a portion of the droplet channel, (iii) the carrier fluid reservoir and/or (iv) the sample reservoir. The energy application device can provide energy to form a skin around an individual droplet of the one or more droplets. In an embodiment, the energy application device is a thermal heating element. In another embodiment, the energy application device is coupled (e.g., physically coupled, thermally coupled) to the intersection and/or the droplet channel, and the energy application device provides energy to form a skin around an individual droplet at the intersection and/or the droplet channel. In another embodiment, the energy application device is coupled to any two of (i)-(iv). In another embodiment, the energy application device is coupled to any three of (i)-(iv). In another embodiment, the energy application device is coupled to each of (i)-(iv). In another embodiment, the system further comprises a computer processor that is programmed to (a) regulate the formation of the one or more droplets by the droplet generator, and/or (b) regulate the application of energy by the energy application device to any one, two, three, or all of (i)-(iv).

In another aspect, an emulsion comprises a plurality of droplets having sample partitions. At least a subset of the droplets are capable of emitting a detectable signal. The emulsion can comprise at most about 70% by volume droplets and at least about 30% by volume oil. In an embodiment, an individual droplet of the plurality of droplets has a skin. In another embodiment, the skin has an area compressibility modulus from about 0.01 mN/meter to 10000 mN/meter at a temperature of about 25° C.

In another aspect, a method for forming droplets each containing a sample or partition thereof comprises (a) generating droplets at an intersection of a first channel and a second channel, the first channel in fluid communication with a carrier fluid reservoir and the second channel in fluid communication with a sample reservoir, wherein the droplets are generated by bringing a carrier fluid from the carrier fluid reservoir in contact with a sample or sample partition from the sample reservoir; (b) sequentially directing the droplets along a droplet channel leading from the intersection to a droplet reservoir; (c) forming a skin around each of the droplets in the droplet channel; and (d) collecting the droplets in the droplet reservoir. The collected droplets can have at most about 67% by volume oil and at most about 33% by volume air. In an embodiment, the carrier fluid is an oil. In another embodiment, the skin is formed by heating an individual droplet at (i) the intersection and/or (ii) along at least a portion of the droplet channel as the individual droplet flows from the intersection to the droplet reservoir. In another embodiment, bringing the carrier fluid from the carrier fluid reservoir in contact with the sample or sample partition from the sample reservoir comprises adjusting the pressure in the droplet reservoir to be lower than the pressure in the sample reservoir and the pressure in the carrier fluid reservoir. In another embodiment, the method further comprises removing the droplets from the droplet reservoir.

Another aspect provides machine executable code in a non-transitory storage medium that, when executed by a computer processor, implements any of the methods above or elsewhere herein.

Another aspect provides machine executable code in a non-transitory storage medium that, when executed by a computer processor, implements a method comprising (a) generating a droplet at an intersection of a first channel and a second channel, the first channel in fluid communication with a carrier fluid reservoir and the second channel in fluid communication with a sample reservoir, wherein the droplet is generated by bringing a carrier fluid from the carrier fluid reservoir in contact with a sample or sample partition from the sample reservoir at the intersection; (b) flowing the droplet along a droplet channel leading from the intersection to a droplet reservoir; and (c) providing thermal energy to the droplet at the intersection, the carrier fluid reservoir and/or the sample reservoir.

Another aspect provides machine executable code in a non-transitory storage medium that, when executed by a computer processor, implements a method comprising (a) generating droplets at an intersection of a first channel and a second channel, the first channel in fluid communication with a carrier fluid reservoir and the second channel in fluid communication with a sample reservoir, wherein the droplets are generated by bringing a carrier fluid from the carrier fluid reservoir in contact with a sample or sample partition from the sample reservoir at the intersection; (b) sequentially directing the droplets along a droplet channel leading from the intersection to a droplet reservoir; and (c) heating the droplets at the intersection, the carrier fluid reservoir and/or the sample reservoir.

Another aspect provides machine executable code in a non-transitory storage medium that, when executed by a computer processor, implements a method comprising (a) generating a droplet at an intersection of a first channel and a second channel, the first channel in fluid communication with a carrier fluid reservoir and the second channel in fluid communication with a sample reservoir, wherein the droplet is generated by bringing a carrier fluid from the carrier fluid reservoir in contact with a sample partition from the sample reservoir at the intersection; (b) flowing the droplet along a droplet channel leading from the intersection to a droplet reservoir; and (c) forming a skin around the droplet at or downstream of the intersection.

Another aspect provides machine executable code in a non-transitory storage medium that, when executed by a computer processor, implements a method comprising (a) generating droplets at an intersection of a first channel and a second channel, the first channel in fluid communication with a carrier fluid reservoir and the second channel in fluid communication with a sample reservoir, wherein the droplets are generated by bringing a carrier fluid from the carrier fluid reservoir in contact with sample partitions from the sample reservoir at the intersection; (b) sequentially directing the droplets along a droplet channel leading from the intersection to a droplet reservoir; (c) forming a skin around each of the droplets in the droplet channel; and (d) collecting the droplets in the droplet reservoir, wherein the collected droplets have at most about 67% by volume oil and at most about 33% by volume air.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGS." herein), of which:

FIGS. 3A-3D schematically illustrate droplet generators having various configurations of energy application zones for forming skins around droplets, in accordance with some embodiments;

FIGS. 4A and 4B schematically illustrate serpentine droplet channels, in accordance with some embodiments;

FIGS. 5A and 5B schematically illustrate a temperature controller adjacent to a droplet channel, in accordance with some embodiments;

FIG. 6A-6C schematically illustrate a system for generating droplets and a droplet cartridge, in accordance with some embodiments;

DETAILED DESCRIPTION

Figure 1A:
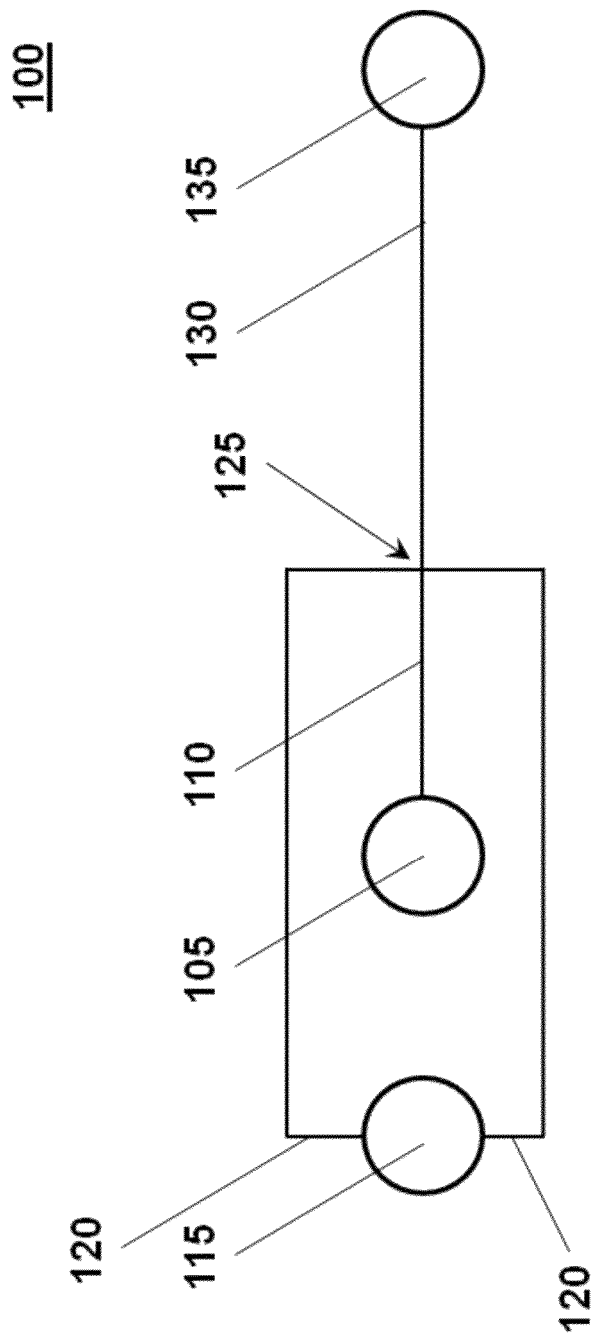
FIG. 1A schematically illustrates a droplet generator.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "channel," as used herein, generally refers to a fluid flow path for conveying matter (e.g., a fluid) from one point to another.

The term "downstream," as used herein, generally refers to the position of a species, such as a droplet, along a system or device(s), such as along a fluid flow path in a droplet generator. A first droplet downstream of a second droplet can be in the same device or a separate device. The devices may or may not be connected, such as by a flow path.

The term "emulsion," as used herein, generally refers to a mixture of two or more fluids that are normally immiscible. An emulsion can include a first phase in a second phase, such as an aqueous phase in an oil phase. In some cases, an emulsion includes more than two phases. It may also include multiple emulsions.

Droplet Stability Control Devices

The present disclosure provides, inter alia, systems and devices for sample preparation, manipulation, partitioning, and/or analysis, particularly systems or devices in which energy is transferred to the device. In some cases, the energy is transferred to a sample partition, such as a droplet.

The system or device may comprise a droplet generator having a first channel in fluid communication with a carrier fluid reservoir and a second channel in fluid communication with a sample reservoir. The first channel and second channel may meet at an intersection that receives a sample (e.g., biological sample, nucleic acid, polypeptide, etc.) from the sample reservoir and a carrier fluid (e.g., oil, aqueous) from the carrier fluid reservoir and generates one or more droplets. In some cases, the droplets may flow along a droplet channel to a droplet reservoir for holding droplets.

The sample reservoir can comprise a sample to be analyzed, reagents for sample processing and detection, such as nucleic acid amplification reagents (e.g., primers, nucleotides, polymerase, probles, oligonucleotides) and/or detection reagents (e.g., fluorescent dye, radio isotopes, magnetic labels, etc.), or any combination thereof. Often, a partition (e.g., droplet) within the system or device comprises one or more of such materials from the sample reservoir. A droplet can include a sample partition, such as a fraction of a sample. For example, the sample may comprise a mixture of nucleic acids (e.g., homogeneous or heterogenous mixture) that is then divided into partitions (e.g., droplets) that contain, on average, less than 5, 4, 3, 2, or 1 nucleic acids. In some cases the sample partition is prepared as a reaction mixture for amplification of a nucleic acid target.

The system or device may further include an energy application device (or member) for coupling energy to a region of the device or system, or to an element (e.g., droplet) within the device or system. The region may be, for example, a partition, a region upstream of the intersection, a sample reservoir, a carrier fluid reservoir, a region downstream of the intersection, a droplet channel (or at least a portion of a droplet channel), and/or droplet reservoir. In some cases, the energy application device (or member) applies energy to a particular partition or set of partitions. The energy may be applied to, for example, a particular droplet or a set of droplets. The energy may be applied randomly or non-randomly. Often, the energy application device applies the energy to a droplet when a droplet reaches a particular location (e.g., downstream of the intersection, at least a portion of the droplet channel, and/or a droplet reservoir for holding droplets). The energy application device may transfer energy to an individual droplet of the one or more droplets at the intersection and/or as the droplet moves along the droplet channel to the droplet reservoir. The energy may be transferred to a specific droplet within a population of droplets, to every droplet, to some droplets, to many droplets, or to most droplets. In some cases, the energy is transferred to different droplets at a particular interval. The energy may be transferred, for example, to droplets at intervals of every other droplet (or every second droplet), every third droplet, every fourth droplet, every fifth droplet, every sixth droplet, or every $10^{th}$ droplet (or at intervals less than or greater than such intervals).

In some situations, a droplet flows through a fluid flow path as an emulsion, which may be characterized by the predominant liquid or type of liquid in separate phases. For example, the phases may be an oil phase and an aqueous phase. In some cases, one or more of the phases may be a fluorous phase. In many situations, the predominant fluids in the emulsion are aqueous and oil. Oil is any liquid compound or mixture of liquid compounds that is immiscible with water and that includes carbon, in some cases high carbon content. In some examples, oil also may have a high content of hydrogen, fluorine, silicon, oxygen, or any combination thereof, among others. For example, any of the emulsions disclosed herein may be a water-in-oil (W/O) emulsion, comprising aqueous droplets in a continuous oil phase. Conversely, any of the emulsions disclosed herein may be oil-in-water (O/W) emulsions. This disclosure also provides multiple emulsions. For example, aqueous droplets may be enveloped by a layer of oil and flow within an aqueous continuous phase. The one or more droplets of the system flow along the droplet channel as an emulsion that may be made up of a plurality of phases.

The oil used in any of the devices or systems described herein may be or include at least one of silicone oil, mineral oil, hydrocarbon oil, fluorocarbon oil, vegetable oil, or a combination thereof, among others. Any other suitable components may be present in any of the emulsion phases, such as at least one surfactant, reagent, sample (or partitions thereof), other additive, preservative, label, dye, particles, or any combination thereof. In some examples, an oil is any liquid compound or mixture of liquid compounds that is immiscible with water and that has a high content of carbon. In some examples, the oil may also have a high content of hydrogen, fluorine, silicon, oxygen, or any combination thereof, among others. For example, any of the emulsions disclosed herein may be a water-in-oil (W/O) emulsion (i.e., aqueous droplets in a continuous oil phase). The oil may, for example, be or include at least one silicone oil, mineral oil, fluorocarbon oil, vegetable oil, or a combination thereof, among others. Any other suitable components may be present in any of the emulsion phases, such as at least one surfactant, reagent, sample (i.e., partitions thereof), other additive, label, particles, or any combination thereof. An example oil formulation is as follows: (1) Dow Corning 5225C Formulation Aid (10% active ingredient in decamethylcyclopentasiloxane)—20% w/w, 2% w/w final concentration active ingredient, (2) Dow Corning 749 Fluid (50% active ingredient in decamethylcyclopentasiloxane)—60% w/w, 30% w/w active ingredient, and (3) Poly(dimethylsiloxane) Dow Corning 200® fluid, viscosity 5.0 cSt (25.degree. C.)—20% w/w.

A surfactant may be characterized as a surface-active agent capable of reducing the surface tension of a liquid in which it is dissolved, and/or the interfacial tension with another phase. A surfactant, which also or alternatively may be described as a detergent and/or a wetting agent, may incorporate both a hydrophilic portion and a hydrophobic portion, which may collectively confer a dual hydrophilic-lipophilic character on the surfactant. A surfactant may be characterized according to a Hydrophile-Lipophile Balance (HLB) value, which is a measure of the surfactant's hydrophilicity compared to its lipophilicity. HLB values range from 0-60 and define the relative affinity of a surfactant for water and oil. Nonionic surfactants can have HLB values ranging from 0-20 and ionic surfactants can have HLB values of up to 60. Hydrophilic surfactants can have HLB values greater than about 10 and a greater affinity for water than oil. Lipophilic surfactants can have HLB values less than about 10 and a greater affinity for oil than water.

In some cases, an emulsion and/or any phase thereof can include at least one hydrophilic surfactant, at least one lipophilic surfactant, or a combination thereof. Alternatively, or in addition to, an emulsion and/or any phase thereof can include at least one nonionic (and/or ionic) detergent. Emulsions of the disclosure may include a surfactant comprising polyethyleneglycol, polypropyleneglycol, or Tween 20, among others.

The energy application device can be an energy source that is coupled to a fluid flow path of the droplet generator, including the intersection, at least a portion of the droplet channel, and/or the droplet reservoir. In some cases, the energy application device is a heat source that is thermally coupled to the fluid flow path. In some cases, the energy application device includes a heating device in thermal communication with the fluid flow path. Alternatively, the energy application device can be a source of electromagnetic radiation, such as such as ultraviolet (UV), infrared (IR), or visible light. In an example, the energy application device is a laser. The energy application device can be removable from the droplet generator.

In some cases, the energy application device is a heating element. The heating element can be a resistive heating element, such as, for example, a heating element comprising one or more elemental metals selected from Ta, Ti and W. In some examples, the heating element can be a stainless steel alloy, a nichrome alloy, or combination thereof. The heating element can have a composition and dimension that is selected to provide a desired heating rate (power) to droplets flowing through the fluid flow path, including the intersection, at least a portion of the droplet channel, and/or a droplet reservoir for holding droplets. In some cases, the heating element is thermally coupled to a fluid flow path with the aid of a heat conductor, such as, for example, a foil comprising copper or a copper alloy.

The heating element can include one or more thermoelectric devices thermally coupled to the fluid flow path. The thermoelectric device can be selected to provide a desired heating rate to droplets flowing through the fluid flow path. The heating rate can be selected to induce skin formation around an individual droplet. In some examples, the heating rate (i.e., the change in temperature with time) is sufficiently rapid to induce skin formation. For instance, the heating rate of a continuous phase can be sufficiently rapid to induce skin formation around one or more droplets. In some examples, one or more droplets are heated up to a temperature of at least about 37° C., 40° C., 45° C., 50° C., 55° C., 60° C., 65° C., 70° C., 75° C., 80° C., 85° C., 90° C., or 95° C. in a time period of about or at least about 0.001 seconds, 0.01 seconds, 0.1 seconds, 0.5 seconds, 1 second, 2 seconds, 3 seconds, 4 seconds, 5 seconds, 10 seconds, 30 seconds, 40 seconds, 50 seconds, 1 minute, 2 minutes, 3 minutes, 4 minutes, 5 minutes, 10 minutes, 30 minutes, or 1 hour to induce skin formation. In other examples, one or more droplets are heated up to a temperature of at least about 37° C., 40° C., 45° C., 50° C., 55° C., 60° C., 65° C., 70° C., 75° C., 80° C., 85° C., 90° C., or 95° C. in a time period that is less than or equal to about 1 hour, 30 minutes, 10 minutes, 5 minutes, 4 minutes, 3 minutes, 2 minutes, 1 minute, 50 seconds, 40 seconds, 30 seconds, 10 seconds, 5 seconds, 4 seconds, 3 seconds, 2 seconds, 1 second, 0.5 seconds, 0.1 seconds, 0.01 seconds, or 0.001 seconds. In some cases, the temperature is maintained at a droplet formation temperature of at least about 37° C., 40° C., 45° C., 50° C., 55° C., 60° C., 65° C., 70° C., 75° C., 80° C., 85°

C., 90° C., or 95° C. for a time period of at least about 0.001 seconds, 0.01 seconds, 0.1 seconds, 0.5 seconds, 1 second, 2 seconds, 3 seconds, 4 seconds, 5 seconds, 10 seconds, 30 seconds, 40 seconds, 50 seconds, 1 minute, 2 minutes, 3 minutes, 4 minutes, 5 minutes, 10 minutes, 30 minutes, or 1 hour to induce skin formation.

In some situations, at a droplet formation temperature, skin formation can occur in a time period of at least about 001 seconds, 0.01 seconds, 0.1 seconds, 0.5 seconds, 1 second, 2 seconds, 3 seconds, 4 seconds, 5 seconds, 10 seconds, 30 seconds, 40 seconds, 50 seconds, 60 seconds, 70 seconds, 80 seconds, 90 seconds, 100 seconds, 200 seconds, 300 seconds, 400 seconds, 500 seconds, or 600 seconds. Skin formation can be the cumulative result of one or more cycles of heating, which cycle can be accompanied by cooling. Skin formation can occur more rapidly at higher temperatures.

In some cases, a skin forms around a droplet by polymeric degradation. Polymeric degradation can include protein denaturation (e.g., albumin denaturation) or nucleic acid denaturation (e.g., DNA denaturation). In some examples, a skin forms upon protein denaturation around a droplet.

An energy application device can include one or more heat spreading elements that direct energy from a source of thermal energy (e.g., resistive heating element) to an area where thermal energy is to be applied or delivered. A heat spreading element can be a material that readily transfers thermal energy from one point to another. In an example, a heat spreading element comprises aluminum either alone or as an alloy. A heat spreading element can have a thermal conductivity that is greater than or equal to about $100\,W\,m^{-1}\,K^{-1}$, $110\,W\,m^{-1}\,K^{-1}$, $120\,W\,m^{-1}\,K^{-1}$, $130\,W\,m^{-1}\,K^{-1}$, $140\,W\,m^{-1}\,K^{-1}$, $150\,W\,m^{-1}\,K^{-1}$, $160\,W\,m^{-1}\,K^{-1}$, $170\,W\,m^{-1}\,K^{-1}$, $180\,W\,m^{-1}\,K^{-1}$, $190\,W\,m^{-1}\,K^{-1}$, $200\,W\,m^{-1}\,K^{-1}$, $250\,W\,m^{-1}\,K^{-1}$, $300\,W\,m^{-1}\,K^{-1}$, $350\,W\,m^{-1}\,K^{-1}$, $400\,W\,m^{-1}\,K^{-1}$, or $450\,W\,m^{-1}\,K^{-1}$. Examples of heat spreading elements include aluminum, which may have a thermal conductivity from about $200\,W\,m^{-1}\,K^{-1}$ to $250\,W\,m^{-1}\,K^{-1}$.

In some embodiments, the system transfers energy to an individual droplet to form a skin around the droplet. In some cases, the system transfers energy to an individual droplet or an emulsion having the droplet in order to avoid or mitigate deterioration of temperature sensitive reagents. Temperature control in some cases can aid in regulating one or more properties of an individual droplet or emulsion, such as the viscosity of a droplet and/or emulsion, or the density of a droplet and/or emulsion. The skin can be formed upon thermally-induced cross-linking, for instance, or by cross-linking upon exposure of a droplet to electromagnetic radiation having a frequency (or energy) capable of inducing cross-linking. The skin can have an area compressibility modulus between about 0.001 mN/meter and 100,000 mN/meter, or 0.01 mN/meter and 10,000 mN/meter at a temperature of about 25° C. In some cases, the area compressibility modulus is greater than or equal to about 0.01 mN/meter, 0.1 mN/meter, 1 mN/meter, 10 mN/meter, 50 mN/meter, 100 mN/meter, 500 mN/meter, 1000 mN/meter, 5,000 mN/meter, 10,000 mN/meter, or 50,000 mN/meter.

In some embodiments, the system transfers heat to an individual droplet to form a skin around the droplet. In some embodiments, the droplet contains a protein, such as bovine serum albumin, which can form a component of the skin (e.g., upon denaturation). In some embodiments, the droplet contains a polymer or other molecule that crosslinks upon exposure to electromagnetic radiation to form a component of the skin. In some embodiments, the electromagnetic radiation is UV radiation.

In some embodiments, the system further includes a third channel in fluid communication with the carrier fluid reservoir. The third channel meets with the first and second channels at the intersection.

In some embodiments, the droplet generator is included in a housing having one or more droplet generators. Without limitation, the housing can comprise any number of structures, including but not limited to one or more modules, cassettes, chips, plates, containers, arrays, or cartridges. The housing can include a plurality of droplet generators for parallel processing, which can aid in maximizing processing efficiency—e.g., a plurality of samples can be partitioned in droplets in parallel, thereby reducing droplet generation time.

In some embodiments, the system includes a pressure source for facilitating the flow of droplets to the droplet reservoir. The pressure source can be a source of positive pressure operatively coupled to the oil and/or sample reservoir, or a source of negative pressure (i.e., vacuum) operatively coupled to the fluid flow path, such as by way of the droplet reservoir. The source of positive pressure can be a compressor or a pressurized fluid, such as a pressurized gas (e.g., pressurized air). The source of negative pressure can be a pumping system comprising one or more pumps, such as mechanical pumps.

The system may be configured for use with nucleic acid amplification, such as polymerase chain reaction (PCR). In some embodiments, during sample processing, an energy application device, which in some cases is the same device use to induce skin formation around the droplets, is used to raise the temperature of droplets to initiate amplification. In some situations, the temperature of the droplets is raised following the formation of a skin around the droplets, as described herein. The system can thermally cycle the temperature of the droplets, from a low temperature to a high temperature, and in some cases to a low temperature with the aid of cooling. Cooling can be implemented with the aid of heat fins, for instance, or a cooling system, such as a thermoelectric cooling system.

In some embodiments, the droplet generator is a removable container having the fluid flow path, including the intersection, droplet channel and the droplet reservoir. The container can be removable from the system. In some cases, the removable container is a consumable, which can be discarded after droplet generation and any subsequent processing and/or analysis.

In some situations, the energy application device comprises an interface plate that is formed of a metallic material. During sample processing, the droplet generator can rest adjacent to the interface plate, which configuration can aid in transferring heat to the droplets upon formation and/or flow through the fluid flow path. The interface plate can be coupled to a source of energy. In some embodiments, the energy source is integrated in the system. In some embodiments, the energy source is external to the system. Examples of energy sources include but are not limited to a resistive heating element, such as an integrated resistive heating element, a water bath, or a thermoelectric heating element, such as a Peltier device.

As an alternative, the energy application device is integrated with the removable container. In an example, the energy application device is a resistive heating element that is formed in the removable container. During sample processing, electrodes of the heating element can be electrically coupled to power terminals of the system.

In some situations, the system includes a detection assembly in fluid communication with the fluid flow path. In some cases, the detection assembly is situated along at least a portion of the droplet channel, between the intersection and the droplet reservoir. The detection assembly can be configured to detect signals from droplets in the fluid flow path, such as upon flowing through the droplet channel. The detection assembly can include an optical sensor or other electronic detector that is sensitive to a select frequency of light. The sensor can be adapted to detect fluorescent emission, for example. In some cases, the detection assembly can include an excitation source, such as a light source that is adapted to induce fluorescence in the fluid. One or more optical elements (e.g., mirrors, lenses) can be provided to direct light emitted from the fluid to the detection assembly, and/or to direct light from a light source to the fluid.

Reference will now be made to the figures, wherein like numerals refer to like parts throughout. It will be appreciated that the figures are not necessarily drawn to scale. The figures are illustrative and are not intended to limit the invention.

Figure 1B:
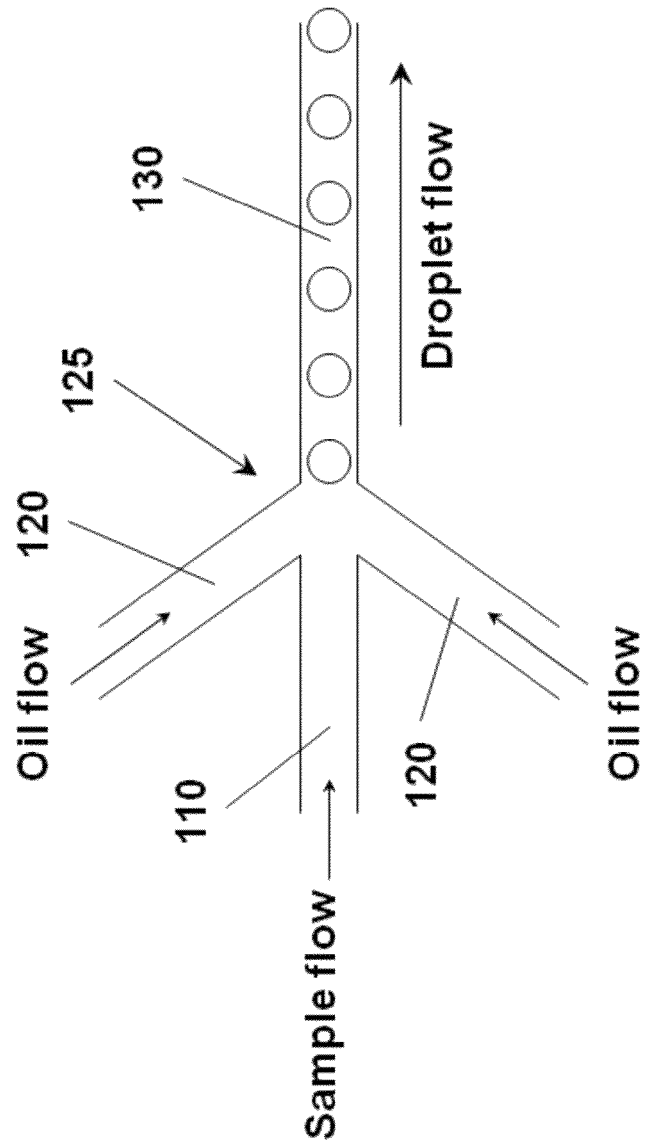
FIG. 1B schematically illustrates droplet formation with the aid of the droplet generator of FIG. 1A.

FIG. 1A shows a droplet generator 100 having a sample reservoir 105 in fluid communication with a sample channel 110, and a carrier fluid reservoir 115 in fluid communication with carrier fluid channels 120. The sample channel 110 and carrier fluid channels 120 meet at a droplet generation point (or intersection) 125. With reference to FIG. 1B, during operation, a carrier fluid (e.g., oil) from the carrier fluid reservoir 115 is directed through the carrier fluid channels 120 to the intersection 125, and a sample from the sample reservoir 105 is directed through the sample channel 110 to the intersection 125, wherein a sample partition, including any processing reagents (e.g., primers, polymerase, dyes) that may be provided from the sample reservoir 105, generate a droplet comprising an aqueous phase in an oil phase. A droplet thus formed flows in a droplet channel 130 from the intersection 125 to a droplet reservoir 135 for holding the droplets. The direction of flow of the sample, oil and droplets are indicated in FIG. 1B.

The sample channel 110 can be perpendicular or non-perpendicular to the carrier fluid channels 120. In some cases, a carrier fluid channel 120 is at an angle from about 10° to 90°, or 25° to 80°, or 40° to 70° with respect to the sample channel 110, or at least about 10°, 15°, 20°, 25°, 30°, 40°, 50°, 60°, 70°, 80°, or 85° with respect to the sample channel 110.

In some cases, a detection system can be provided along the droplet channel 130 to aid in detecting one or more samples in the droplets. In some cases, the detection system includes an excitation light source and a detector for detecting light emitted from a droplet following excitation. In still other cases, the detection of the droplets may occur at a point downstream, such as after the droplets have exited the droplet channel. For example, the detection may occur in a droplet reservoir, or after the droplets exit the droplet reservoir.

Figure 2:
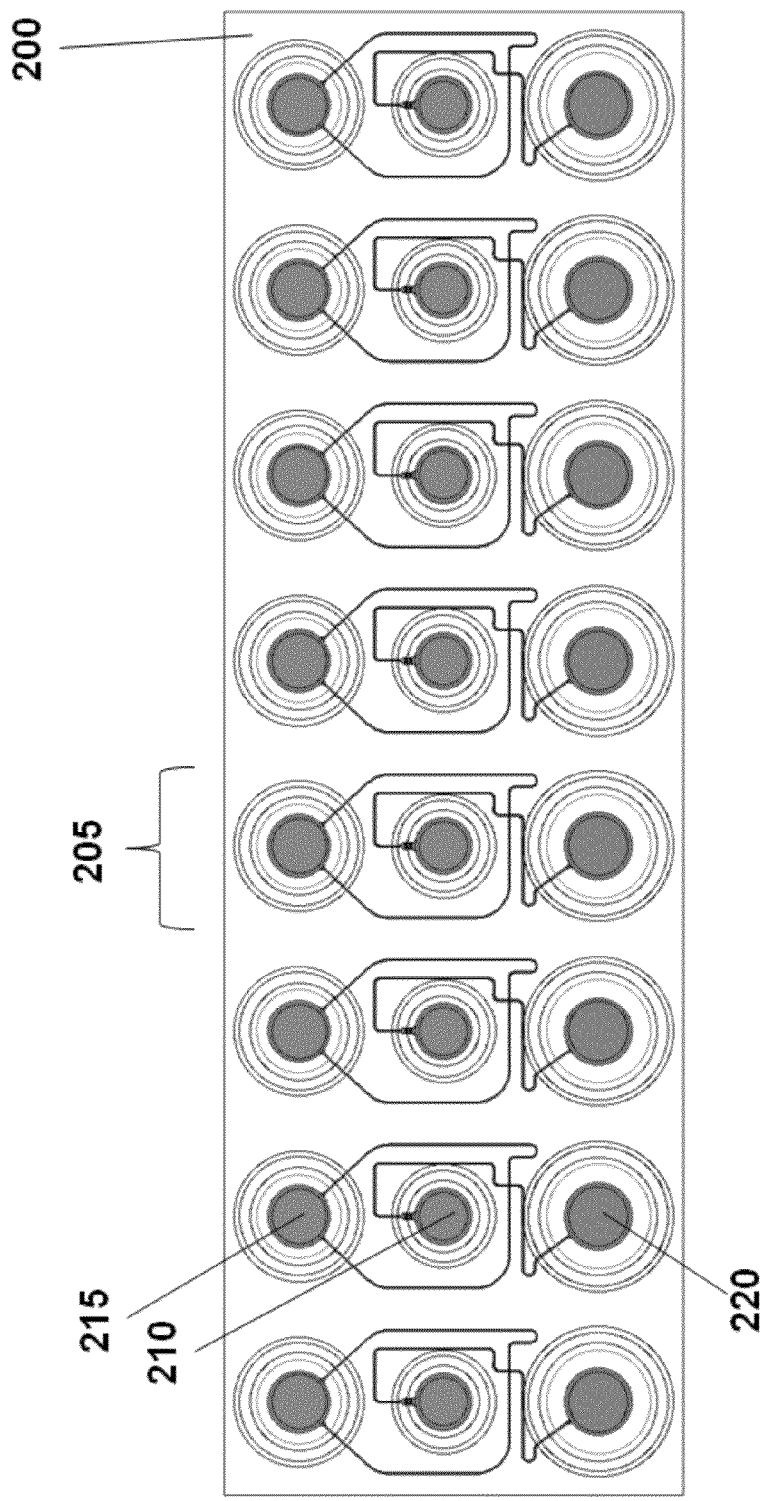
FIG. 2 shows a droplet cartridge having a plurality of droplet generators.

The droplet generator 100 can be formed in a single-piece or multi-piece substrate. The substrate can include 1, 2, 3, 4, 5, 6, 7, 8, 9, 10, 20, 25, 30, 40, 45, 50, 100, 500, or more droplet generators. In some cases, the substrate is a consumable cassette (or cartridge) that is configured to be inserted and removed from a system for droplet generation. In an example, FIG. 2 shows a substrate 200 having eight individual droplet generators 205 formed therein. Each droplet generator 205 includes a sample reservoir 210, carrier fluid reservoir 215 and droplet reservoir 220.

A droplet generator can include an energy application device for providing energy to a droplet to provide droplet stability. In some embodiments, the droplet generator is coupled to a separate energy application device. For example, the droplet generator can be a disposable, single-use device that is coupled to a reusable system that contains the energy application device. In some cases, droplet stability is provided by inducing skin formation, which aids in maintaining the structural integrity of the droplet upon formation, subsequent flow through a droplet channel, and storage in a droplet reservoir.

The energy application device can be coupled to the droplet generator through one or more energy application zones. In an example, a droplet generator includes one or more heating zones for applying thermal energy to a droplet, which can aid in inducing skin formation, or other thermal-dependent process. The heating zones can be isolated from one another with the aid of insulators, such as an insulating polymeric material, or cooling zones.

An energy application zone can be coupled to one or more of the droplet generation point, the droplet channel, the droplet reservoir, the sample reservoir and the carrier fluid reservoir. In some cases, the energy application zone is a portion or region of such aspects of the device, such as a portion of the droplet channel. In some cases, a droplet generator can include a plurality of energy application zones, with each zone coupled to at least one of the droplet generation point, the droplet channel, the droplet reservoir, the sample reservoir and the carrier fluid reservoir.

In some situations, an energy application zone is coupled to the droplet generation point (or intersection). This can aid in applying energy to a droplet at the moment it is formed. In some cases, the droplets are contacted with the energy for a certain duration of time, while the droplets are within a droplet generation point, e.g., a period of less than 0.1 seconds, 0.5 seconds, 1 second, 2 seconds, 3 seconds, 4 seconds, 5 seconds, 10 seconds, 30 seconds, 40 seconds, 50 seconds, 1 minute, 2 minutes, 3 minutes, 4 minutes, 5 minutes, 10 minutes, 30 minutes, or 1 hour. In some cases, the droplets are contacted with the energy for a certain duration of time, while the droplets are within any region of the generator, e.g., a period of at least 0.1, 0.5, 1, 2, 3, 4, 5, 6, 7, 8, 9, 10, 20, 30, 40, 50 or more seconds, or at least 1, 2, 3, 4, 5, 10, 20, 30, 40, 50, 60 or more minutes.

In other situations, an energy application zone is coupled to at least a portion of the droplet channel. This can aid in applying energy to a droplet between the point it is formed at the droplet generation point and the point it is stored in the droplet reservoir or, alternatively, directed to a droplet reader. In some cases, the droplets are first contacted with the energy in a droplet channel for a particular length of time, such as less than about 0.1 seconds, 0.5 seconds, 1 second, 2 seconds, 3 seconds, 4 seconds, 5 seconds, 10 seconds, 30 seconds, 1 minutes, 10 minutes, 30 minutes, or 1 hour after formation.

In other situations, an energy application zone is coupled to the droplet reservoir, which can aid in applying energy to a droplet while it is in the droplet reservoir. The energy zone coupled to the droplet reservoir can also aid in initiating nucleic acid polymerization, such as polymerase chain reaction (PCR). In another example, an energy application point is coupled to the sample reservoir and/or the carrier fluid (e.g., oil) reservoir. Such a configuration can aid in providing energy to the sample and/or the carrier fluid, which energy can subsequently be used in inducing skin formation upon droplet generation, or other thermal-sensitive application.

Figure 3A:
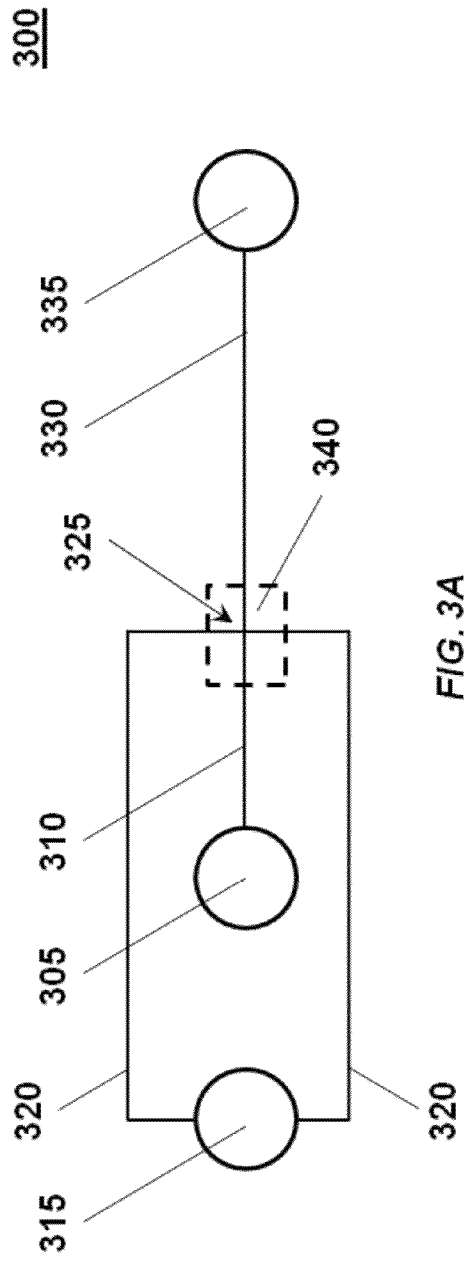

FIGS. 3A-3D illustrate exemplary energy application zones, as may be used with droplet generators provided herein, such as the droplet generator 100 of FIG. 1A. Energy application zones in the figures are indicated by rectangles with dashed sides. FIG. 3A shows the droplet generator 300 having a sample reservoir 305, sample channel 310, carrier fluid reservoir 315, carrier fluid channels 320, a droplet generation point 325, droplet channel 330 and a droplet reservoir 335. The droplet generator may include an energy application zone 340 coupled to the droplet generation point 325. The energy application zone 340 may be in communication (e.g., thermal communication) with an energy source, such as a resistive heater.

Figure 3B:
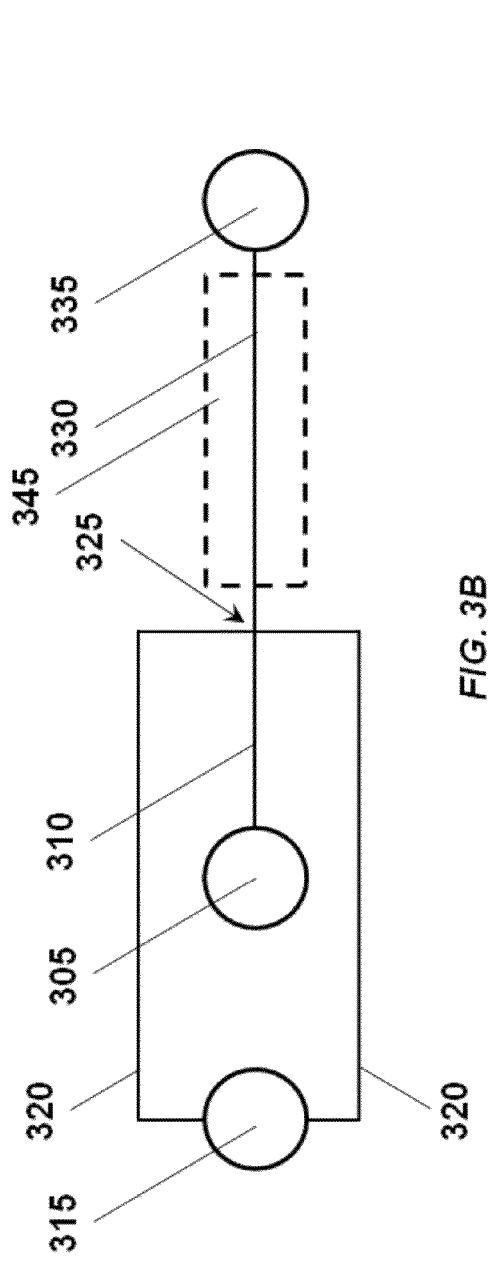

FIG. 3B shows the droplet generator 300 having an energy application zone 345 coupled to the droplet channel 330. FIG. 3C shows the droplet generator 300 having an energy application zone 350 coupled to the droplet generation point 325 and the droplet channel 330. FIG. 3D shows the droplet generator 300 having an energy application zone 355 coupled to the droplet generator 300 in its entirety, including the sample reservoir 305, carrier fluid reservoir 315, the droplet generation point 325, the droplet channel 330, and the oil reservoir 335.

Energy application zones are coupled to an energy source, such as a source of infrared (IR) light, a resistive heating element or a convective energy source, such as a warm fluid. In an example, the energy application zone 340 of FIG. 3A includes an IR light source that is in optical communication with the droplet generation point 325, such as, for example, with the aid of mirrors and focusing optics. In another example, the energy application zone 345 of FIG. 3B includes a resistive heating element in thermal communication with the droplet channel 330.

In an exemplary implementation of droplet generators with energy application devices, droplets are formed with the aid of the droplet generator 300 of FIG. 3B having the energy application zone 345 along the droplet channel 330. The energy application zone is in thermal communication with a resistive heating element, which includes one or more metals (e.g., tantalum, titanium) in electrical communication with an electrical power source. During use, a sample from the sample reservoir 305 and oil from the carrier fluid reservoir 315 are directed to the droplet generation point 325, at which point some of the sample comes in contact with the carrier fluid to form a droplet. A droplet thus formed includes a sample partition, and reagents for sample processing, such as, for example, nucleic acid amplification and detection reagents (e.g., primer, polymerase, nucleotides and fluorescent dye). The droplet then flows through the droplet channel 330 to the droplet reservoir 335. As the droplet flows along the droplet channel 330 from the droplet generation point 325 to the droplet reservoir 335, the droplet is heated upon the application of thermal energy from the energy application member to the energy application zone 345. This induces skin formation around the droplet, which is stored in the droplet reservoir 335.

In some embodiments, the droplet generator 300 as a whole is heated, such as to induce skin formation. Heating the droplet generator 300 can heat the channels of the droplet generator, including the fluid in the channels. The droplet generator 300 can include multiple sub-systems, each comprising a droplet generation point 325 and droplet channel 330. The sub-systems can be provided in a parallel configuration (see FIG. 2). Heating the droplet generator 300 can enable the sub-systems to be heated simultaneously, which can enable the formation of skins around droplets in each of the sub-systems.

In some cases, energy application zones can include the sample reservoir 305, the carrier fluid reservoir 315, the channel leading from the sample reservoir to the droplet generation point 325, and/or one or both of the channels leading from the carrier fluid reservoir 315 to the droplet generation point 325.

Often, the devices described herein facilitate skin formation on a droplet. For example, the application of energy such as heat may trigger the development of skin around a droplet. The droplet thus formed having a skin may be advantageously more stable in view of fluid perturbations and shear forces, as may be applied upon transport of the droplet for further processing or analysis, such as a temperature regulator for nucleic acid amplification or a droplet detector for detecting the sample in the droplet. In some cases, a droplet with a skin is capable of withstanding shear forces or other mechanical perturbations for a time period of at least about 1 second, 10 seconds, 30 seconds, 1 minute, 10 minutes, 30 minutes, 1 hour, 2 hours, 3 hours, 4 hours, 5 hours, 6 hours, or more.

Temperature regulation and/or the application of energy may have other purposes. In some examples, the temperature of a carrier fluid, sample fluid and/or emulsion containing a droplet may be maintained substantially uniform so as to, for example, avoid destruction, activation, deactivation of temperature-sensitive enzymes, or to minimize, if not prevent, the destruction of temperature-sensitive reagents. Temperature regulation may also be used to adjust various fluid properties, such as fluid viscosity.

In some embodiments, droplets with skins are more robust than droplets without skins. In some embodiments, droplets with skins are less likely to coalesce when placed in close proximity to one another, compared to droplets without skins. In some situations, droplets with skins have increased stability (as characterized by the probability of droplet disruption upon mechanical perturbation) of at least about 5%, 10%, 20%, 30%, 40%, 50%, 60%, 70%, 80%, 90%, or 95% in relation to droplets without skins.

In some cases, a droplet channel leading from a droplet generation point to a droplet reservoir or a droplet detector has a cross section that is circular, triangular, oval, square-like, rectangular, trapezoidal, or pentagonal. The size and/or shape of the cross section can be consistent along the length of the droplet channel, or can vary over the length of the droplet channel. In some embodiments, the droplet channel is linear, curved, angled, planar, non-planar curvilinear (or serpentine), or some combination thereof. Often, the serpentine channel is planar. Such a serpentine droplet channel ("serpentine channel") can increase the residence time of a droplet in a select portion of the droplet generator, such as in an energy application zone. This can aid in applying energy to a droplet to induce skin formation while reducing the size of the droplet channel and, thus, the droplet generator, the size of which can depend on the size of the droplet channel. Additionally, or alternatively, the serpentine channel can facilitate droplet mixing, as may be the case if droplets from a plurality of droplet generators brought to a mixing point for mixing. In such a case, increasing the residence time of such a mixture of droplets can provide for a more uniform mixture of droplets. The shape of the flow path of a serpentine channel can be configured to provide a desired flow resistance, a desired residence time, a desired mixing rate, or the like.

The path of the droplet channel can be substantially linear. In some embodiments, the path of the droplet channel can comprise one or more meanders. A meander can be a section of droplet path that does not take the shortest path between two points. The one or more meanders can be in series, in parallel, or a combination of series and parallel. The meanders can be configured to provide a desired or otherwise predetermined flow resistance, a desired residence time, a desired mixing, or the like.

FIG. 4A shows a serpentine droplet channel 400, in accordance with some embodiments of the present disclosure. The channel 400 includes an entry port 405 from a droplet generation point (e.g., the droplet generation point 125 of FIG. 1A), an exit port 410 downstream of the entry port 405, and a fluid flow path 415 leading from the entry port 405 to the exit port 410. The fluid flow path 415 includes multiple loops (or bends) 420, which are in fluid communication with entry channels 425a and exit channels 425b in fluid communication with the fluid flow path 415. During use, droplets can enter the fluid flow path 415 through the entry port 405. At least a subset of the droplets can flow through a loop 420 by flowing through an entry channel 425a and subsequently flowing through a loop 420 to an exit channel 425b. From the exit channel 425b the subset of the droplets can enter the fluid flow path 415, and subsequently exit the droplet channel and, in some cases, flow through another loop 420. For instance, a droplet can enter a first loop through a first entry channel, re-enter the fluid flow path 415 through a first exit channel, and flow through a second loop through a second entry channel. Fluid entry to the loops from the fluid flow path 415 can be regulated with the aid of valves, although in some cases, no valves are used. The droplets can leave the droplet channel 400 through the exit port 410. Such a configuration can permit multiple heating zones in the droplet channel 400, with each entry channel 425a, loop 420 and exit channel 425b comprised in a zone. With reference to FIG. 4B, as an alternative, the entry channels 425a and exit channels 425b are precluded, and the fluid flow path 415 directs droplets from the entry port 405 to the exit port 410 through a plurality of loops 420.

The number of loops can be selected to provide a residence time as desired. In some embodiments, a droplet channel includes at least 1, 2, 3, 4, 5, 6, 7, 8, 9, 10, 100, 200, 300, 400, or 500 loops. In some examples, the loops have lengths between about 0.5 micrometers and 100 centimeters, and diameters between about 0.5 micrometers and 100 centimeters.

The flow rate of droplets through the loops and/or heating rate in the droplet channel can be selected to induce skin formation and avoid initiating nucleic acid amplification (e.g., PCR). For example, the droplets may be heated to a temperature sufficient to induce skin formation (e.g., 55° C.) but insufficient to cause significant DNA denaturation. In some cases, however, the flow rate and/or heating rate can be selected to induce skin formation and initiate nucleic acid amplification.

In some examples, one or more droplets flow along a droplet channel at a flow rate between about 0.5 microliter/minute and 10,000 microliters/minute, or 1 microliter/minute and 5,000 microliters/minute. The flow rate can be computed by the relationship: number of droplets/time*average volume (µl)/droplet. Energy may be provided to the one or more droplets under flow.

In some examples, an individual droplet flows at Weber number of 1 or less. The Reynolds number of an individual droplet in an emulsion, or a plurality of droplets in the emulsion, may be less than about 2100, or in some cases greater than 2100. In some cases, the Reynolds number is between about 0.1 and 2100, or 1 and 2000, or 10 and 1000. As an alternative, the Reynolds number is greater than or equal to about 2100, 2200, 2300, 2400, 2500, 3000, 4000, 5000, 6000, 7000, 8000, 9000, or 10,000.

Energy may be applied to droplets to stabilize the droplets. Droplet stabilization may include skin formation, which may aid in preventing droplets from coalescing. In some examples, droplet stabilization aids in preventing 1%, 2%, 3%, 4%, 5%, 10%, 15%, 20%, 25%, 30%, 35%, 40%, 45%, 50%, 60%, or more of a population of 5, 10, 15, 20, 30, 40, 50, 100, 500, 1000, 5000, 10000, 50000, 100000, 500000, 1000000, 10000000, 50000000, 100000000, 500000000, 1000000000, or more droplets from coalescing.

With continued reference to FIGS. 4A and 4B, the droplet channel 400 is formed in a substrate 430 that can be formed of a material with a predetermined thermal conductivity, which may be selected to provide a desirable heating rate of the droplets as they flow through the fluid flow path 415. In some cases, the substrate 430 includes a polymeric material, such as a thermosetting polymer. In other cases, the substrate 430 is formed of a composite material. The substrate 430 in some cases can include a metallic material, in which case the fluid flow path 415 can be optionally coated with a layer of a non-reactive or otherwise inert material. In an example, the substrate 430 includes copper or a copper alloy, and the fluid flow path 415 as well as other channels and loops (e.g., loop 420) that come in contact with a fluid are coated with a nitride or oxide, such as silicon nitride. In another example, the substrate 430 includes a semiconductor, such as silicon, and the fluid flow path 415 is coated with a nitride or oxide, such as silicon nitride.

In some embodiments, the droplet channel 400 is formed in a metallic substrate 430. In such a case, heat can be applied to a droplet as it flows along the fluid flow path 415 by directing a current (e.g., alternating current) through the substrate 430, such as from a first electrode to a second electrode of the substrate 430.

The fluid flow path 415 and other channels and loops (e.g., loop 420) can be formed in the substrate 430 by various manufacturing techniques, such as machining, lithography, injection molding, or imprinting. In cases in which the substrate 430 includes a semiconductor, the fluid flow path 415 can be formed by photolithography. In cases in which the substrate is formed of a metallic material, the fluid flow path 415 can be formed by lithography or imprinting.

The droplet channel 400 can be formed in the same substrate having other components of a droplet generator, such as a sample reservoir, carrier fluid reservoir and droplet reservoir. For instance, the sample reservoir, carrier fluid reservoir and droplet reservoir can be formed in the substrate 430.

With reference to FIGS. 4A and 4B, the droplet channel 400 can be configured for isothermal or gradient mode heating. In isothermal mode, the temperature of the droplet channel 400 is kept constant. In gradient mode, the droplet channel 400 can have various temperature zones, with each zone having a different temperature than another zone. This can enable a droplet to be gradually heated as the droplet flows along the fluid flow path 415.

The droplet channel 400 can permit droplet mixing, which may be used to mix multiple populations of droplets (e.g., a population having droplets with sample partitions and a population having a control sample) to provide a uniform population of droplets. Such uniformity can provide for improved droplet detection with the aid of a droplet detector. Examples of droplet detectors are provided in U.S. Patent Publication No. 2010/0173394 to Colston et al. ("Droplet-based assay system"), which is entirely incorporated herein by reference for all purposes.

The droplet channel 400 can define a single energy application zone of a droplet generator having the droplet channel 400. In some cases, the droplet generator can include a plurality of energy application zones, such as an energy application zone at a droplet generation point (see, e.g., FIGS. 3A-3D).

Energy can be coupled to droplet channels with the aid of various energy application devices, such as resistive heating elements that can be in thermal communication with heating blocks. Alternatively, energy can be coupled with one or more of a radiative energy source and a convective energy source, which may be used in conjunction with one another and/or a conductive energy source, such as a resistive heating element.

Figure 5A:
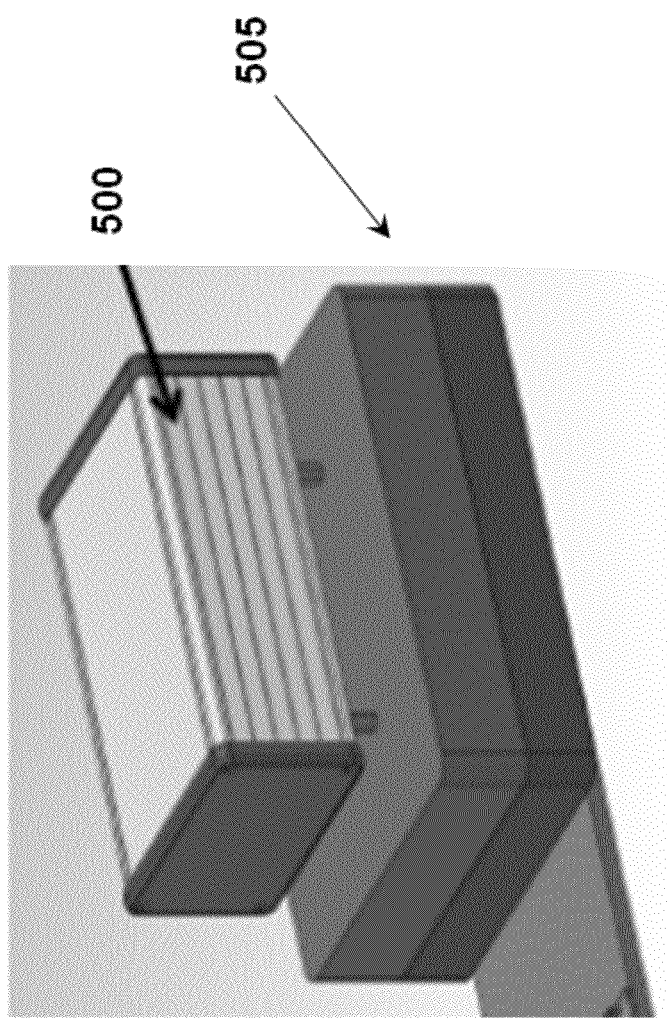

FIGS. 5A and 5B show perspective side and perspective exploded views, respectively, of a temperature controller 500 adjacent to an enclosure 505 having a droplet channel 510, in accordance with some embodiments of the present disclosure. The temperature controller 500 and enclosure 505 can be disposed adjacent to a droplet intersection and other components for forming droplets, such as a sample reservoir and carrier fluid reservoir, as described elsewhere herein. The enclosure 505 has a first portion 505a and a second portion 505b that is adjacent to the first portion. The second portion 505b of the enclosure has the droplet channel 510. The droplet channel 510 includes a serpentine loop 515 with bends (or loops) for increasing the residence time of a droplet in the droplet channel 510. A heating block 520 is adjacent to the droplet channel 510. During use, the temperature controller 500 applies an electrical potential to the heating block 520, which generates heat that is transmitted to the droplet channel 510. The droplet channel 510 is heated to a predetermined temperature, as may be stored in a memory location of the temperature controller 500 and used to regulate the temperature of the droplet channel, as may be measured with the aid of a thermocouple or pyrometer (not shown). During droplet generation, droplets flow through the droplet channel 510 and are heated to induce skin formation around the droplets.

In some embodiments, the carrier fluid-to-air ratio can be selected to improve droplet stability, as may be characterized by the probability of droplet disruption (e.g., rupture) upon the application of a mechanical perturbation. In some situations, an emulsion comprises a plurality of droplets having sample partitions. The droplets can have skins formed as described elsewhere herein. At least some or a subset of the droplets are capable of emitting a detectable signal, such as upon excitation. The emulsion is directed to a droplet reservoir for droplet storage. In the droplet reservoir, the emulsion comprises at most about 70% by volume droplets and at least about 30% by volume a carrier fluid (e.g., oil).

In some embodiments, the emulsion may be directed to a droplet reservoir. The reservoir may contain the emulsion (e.g., droplets plus carrier fluid) and may also contain a volume of air, such as in the headspace of the reservoir. In some embodiments, the stability of the droplets may be further enhanced by selecting specific amounts of carrier and air that are effective for enhancing droplet stability. In some embodiments, decreasing the amount of carrier fluid in the droplet reservoir can enhance droplet stability. In other embodiments, increasing the amount of carrier in the droplet reservoir can enhance droplet stability.

In some embodiments, a method for forming droplets containing sample partitions comprises generating droplets at a droplet intersection, as described elsewhere herein, and forming a skin around each of the droplets at the intersection and/or in the droplet channel. The droplets are then collected in a droplet reservoir. The droplets may be collected in a manner such that they have at most about 10%, 20%, 30%, 40%, 50%, 60%, or 70% by volume oil, and at most about 1%, 5%, 10%, 15%, 20%, 25%, 30%, or 35% by volume air. In an example, the droplets may be collected in a manner such that they have at most about 67% by volume oil and at most about 33% by volume air.

In some cases, droplets are formed with an oil-to-sample ratio of at least about 0.5:1, 1.1:1, 1.5:1, 2:1, 3:1, 4:1, or 5:1. Upon collection in a droplet (or collection) reservoir, the oil-to-droplet ratio, by volume, may be at least about 0.5:1, 1.1:1, 1.5:1, 2:1, 3:1, 4:1, or 5:1. In cases in which a droplet reservoir is open (e.g., to air), the volume of air may be continuous above the droplets. In cases in which the droplet reservoir is sealed or otherwise not open, the ratio of air and droplet may vary. In some example, such as in cases in which a sealed or capped 250 microliter well on a 96-well plate is used, the droplet reservoir may have 200 microliters of air and the remaining 50 microliters may be occupied by a combination of droplets and excess oil (or the continuous phase).

Droplet Formation

This disclosure also provides methods for using a droplet generator to form a droplet containing a sample or sample partition for subsequent processing and/or analysis. The droplet generator comprises a first channel, second channel and droplet channel, which meet at a droplet generation intersection. The first channel may be in fluid communication with a sample reservoir and the second channel may be in fluid communication with a carrier fluid reservoir for supplying a carrier fluid (e.g., oil). A droplet may be generated at the intersection by bringing a carrier fluid (e.g., oil) from the carrier fluid reservoir in contact with a sample partition from the sample reservoir. In cases in which the sample includes a nucleic acid (e.g., DNA, RNA), the sample partition may be prepared as a reaction mixture for amplification of a nucleic acid target. The droplet is then flowed along a droplet channel leading from the intersection to a droplet reservoir for storage. The droplet may be heated at (i) the intersection, (ii) along at least a portion of the droplet channel as the droplet flows from the intersection to the droplet reservoir, and/or when the droplet is in the droplet reservoir.

The carrier fluid and the sample partition are induced to flow from their respective reservoir to the intersection with the aid of positive pressure supplied to the sample reservoir and/or the carrier fluid reservoir, or negative pressure (vacuum) supplied to the droplet reservoir. In some cases, both positive and negative pressure is used to facilitate the flow of fluid to the intersection and subsequent flow of droplets to the droplet reservoir.

In some embodiments, upon heating the droplet, a skin (or shell) is formed around the droplet. In some cases, the skin is formed by heating a droplet for a time period that is sufficient to form the skin, but not induce nucleic acid amplification.

In some cases, a droplet is heated using a heating member in thermal communication with the intersection, at least a portion of the droplet channel, and/or the droplet reservoir. In some cases, a skin is formed by heating a carrier fluid and/or sample partition of the droplet prior to droplet formation, in addition to heating the intersection, at least a portion of the droplet channel, and/or the droplet reservoir. The heating member transfers heat to the droplet as the droplet moves along the droplet channel to the droplet reservoir.

Heating can be implemented with the aid of a resistive heating element, convective heating device, and/or radiative heating device. In an example, heat is applied with the aid of a resistive heating element in thermal communication with the droplet channel and/or the droplet intersection. In another example, heat is applied with the aid of an IR light source in optical communication with the droplet channel and/or the droplet intersection.

Following formation, one or more droplets with samples or sample partitions flow along the droplet channel as an emulsion. The flow rate of the emulsion can be selected to facilitate skin formation.

In some cases, as a droplet flows from the droplet intersection point to the droplet reservoir or a droplet detection region, the temperature of the droplet channel or a reservoir in fluid communication with the droplet channel is cycled to induce nucleic acid amplification. This can advantageously enable in-line nucleic acid amplification prior to sample detection. In some cases, prior to temperature cycling, the droplet is heated to induce skin formation around the droplet.

The droplet may be stabilized by applying energy to the droplet. In some cases, the droplet is stabilized by forming a skin around the droplet. Skin formation can prevent the droplet from coalescing with one or more other droplets.

In some examples, the droplet is stabilized by heating (e.g., incubating) the droplet at a temperature between about 1° C. and 100° C., or 4° C. and 99° C., or 30° C. and 80° C., or 50° C. and 65° C., or 55° C. and 60° C., for at least 0.1, 1, 2, 3, 4, 5, 6, 7, 8, 9, 10, 20, 30, 40, 50, 60, 70, 80, 90, 100, 200, 300, 400, 500, or 1000 seconds. In an embodiment, the droplet is stabilized by heating the droplet at a temperature between about 50° C. and 65° C. for 5 or more seconds. In another embodiment, the droplet is stabilized by heating the droplet at a temperature between about 30° C. and 80° C. for a time period between about 5 seconds and 2 hours. In another embodiment, the droplet is stabilized by heating the droplet at a temperature between about 80° C. and 95° C. for a time period between about 5 seconds and 30 minutes.

In some situations, during skin formation the droplet can be heated along a temperature gradient. The temperature can have a first temperature at a first portion of the droplet channel and a second temperature at a second portion of the droplet channel downstream of the first portion. The temperature gradient can have temperatures from about 55° C. and 98° C. In an example, the temperature at the first portion is 55° C. and the temperature at the second portion is 75° C., and the temperature from the first portion to the second portion is increased (e.g., gradually increased) from 55° C. to 75° C.

Alternatively, the droplet can be heated at a constant temperature for a time sufficient to induce skin formation. In an example, the droplet is heated at a temperature from about 55° C. and 98° C. for a time period from about 1 second to 15 minutes.

In some cases, droplets are subjected to a sequence of temperatures to enable a reaction in at least one, some, or all of the droplets. Such reaction can include PCR, reverse transcription polymerase chain reaction (RT-PCR), isothermal amplification, in vitro translation, or a combination thereof. In some examples, droplets are subjected to a sequence of temperatures to enable an amplification reaction, such as a PCR reaction (e.g., a denaturation temperature, an annealing temperature, and an extension temperature). The temperatures may be optimized for a particular assay. Exemplary denaturation temperatures may be 94° C.-96° C. Exemplary annealing temperatures may be 37° C.-75° C., e.g., 37, 40, 45, 50, 55, 60, 65, 70, or 75° C. Exemplary extension temperatures may be 60-72°, e.g., 60, 61, 62, 63, 64, 65, 66, 67, 68, 69, 70, 71, or 72° C. In some cases, the droplets are subjected to temperature to enable hot-start of an enzyme, such as a polymerase. An exemplary temperature for enabling hot-start is about 95° C.

In some cases, a skin is formed around a droplet by providing energy to the carrier fluid and/or sample prior to droplet formation. The carrier fluid and/or the sample can be heated with the aid of a resistive heating element, for example, or an IR light source that is in optical communication with the carrier fluid reservoir and/or the sample reservoir.

In some embodiments, a skin is formed around a droplet by heating an oil in the carrier fluid reservoir such the oil, upon flowing from the carrier fluid reservoir to the droplet intersection, has a Reynolds number of at least about 1, 10, 1000, 2000, 3000, 4000, 5000 or higher.

Samples

Samples used in the present devices, systems, and/or methods can be any type of sample. In addition, the system or device can be configured for use with any such samples. The sample may be a biological sample. In some cases, the biological sample is analyzed in order to aid the diagnosis or treatment of a subject with a medical condition. The sample may comprise tissue, surgical biopsy, bodily fluid, cells, nucleic acids or polynucleotides (e.g., deoxyribonucleic acid (DNA), ribonucleic acid (RNA)), protein, polypeptides, synthetic polynucleotide, synthetic polypeptide, amino acids, nucleotides, small molecule, or any other compound or molecule. The sample may also comprise reagents for sample analysis (e.g., buffers, probes, enzymes, polymerases, dNTPs, ddNTPs, molecular identifiers, molecular bar codes, labels, fluorescent labels, fluorescent dyes, radio-labels, etc.). Fluorescent labels may be attached to a material, or provided in a free form. For example, the fluorescent label may be attached to a probe (e.g., oligonucleotide probe) or bead. In some cases, the fluorescent label is provided as a free dye, such as a fluorescent dye capable of intercalating a nucleic acid (e.g., Sybr, Sybr green). Exemplary fluorescent labels that can be used in the present systems, devices and methods include but are not limited to DAPI, 5-FAM, 6-FAM, 5(6)-FAM, 5-ROX, 6-ROX, 5,6-ROX, 5-TAMRA, 6-TAMRA, 5(6)-TAMRA SYBR, TET, JOE, VIC, HEX, R6G, Cy3, NED, Cy3.5, Texas Red, Cy5, Cy5.5, SYBR Green, fluorescein derivatives, carboxyfluorescein (FAM), PULSAR 650 dye (a derivative of Ru(bpy)3). In some cases, a quencher dye is used. For example, carboxyfluorescein can be paired in a probe with BLACK HOLE Quencher™ 1 dye, and PULSAR 650 dye can be paired in a probe with, for example, BLACK HOLE Quencher™ 2 dye.

Often, the sample is derived from a human. In some cases, the sample is derived from a mammal, non-human mammal, monkey, ape, chimpanzee, reptile, amphibian, avian, bird, rodent, microbe (e.g., bacterium, virus, fungus), or yeast. In some cases, the sample is chemically synthesized or derived from a recombinant organism, such as a recombinant bacterium or virus.

The following are non limiting examples of polynucleotides or nucleic acids: DNA, RNA, coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, dNTPs, ddNTPs, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component. Polynucleotide sequences, when provided, are listed in the 5' to 3' direction, unless stated otherwise.

Nucleic acids or polynucleotides can be double- or triple-stranded nucleic acids, as well as single-stranded molecules. In double- or triple-stranded nucleic acids, the nucleic acid strands need not be coextensive, for example, a double-stranded nucleic acid need not be double-stranded along the entire length of both strands.

Nucleic acid or polynucleotide generally refers to naturally occurring and non-naturally occurring nucleic acids, as well as nucleic acid analogs that function in a manner similar to the naturally occurring nucleic acids. The nucleic acids may be selected from RNA, DNA or nucleic acid analog molecules, such as sugar- or backbone-modified ribonucleotides or deoxyribonucleotides. Other nucleic analogs, such as peptide nucleic acids (PNA) or locked nucleic acids (LNA), are also suitable. Examples of non-naturally occurring nucleic acids include: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), 2-amino-6-"h"-purines, 6-amino-2-"h"-purines, 6-oxo-2-"h"-purines, 2-oxo-4-"h"-pyrimidines, 2-oxo 6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines. A nucleic acid can encompass any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

Nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

Computer Systems

Provided herein are computer systems for implementing methods of the present disclosure, such as droplet formation, droplet heating, and skin formation.

Figure 8:
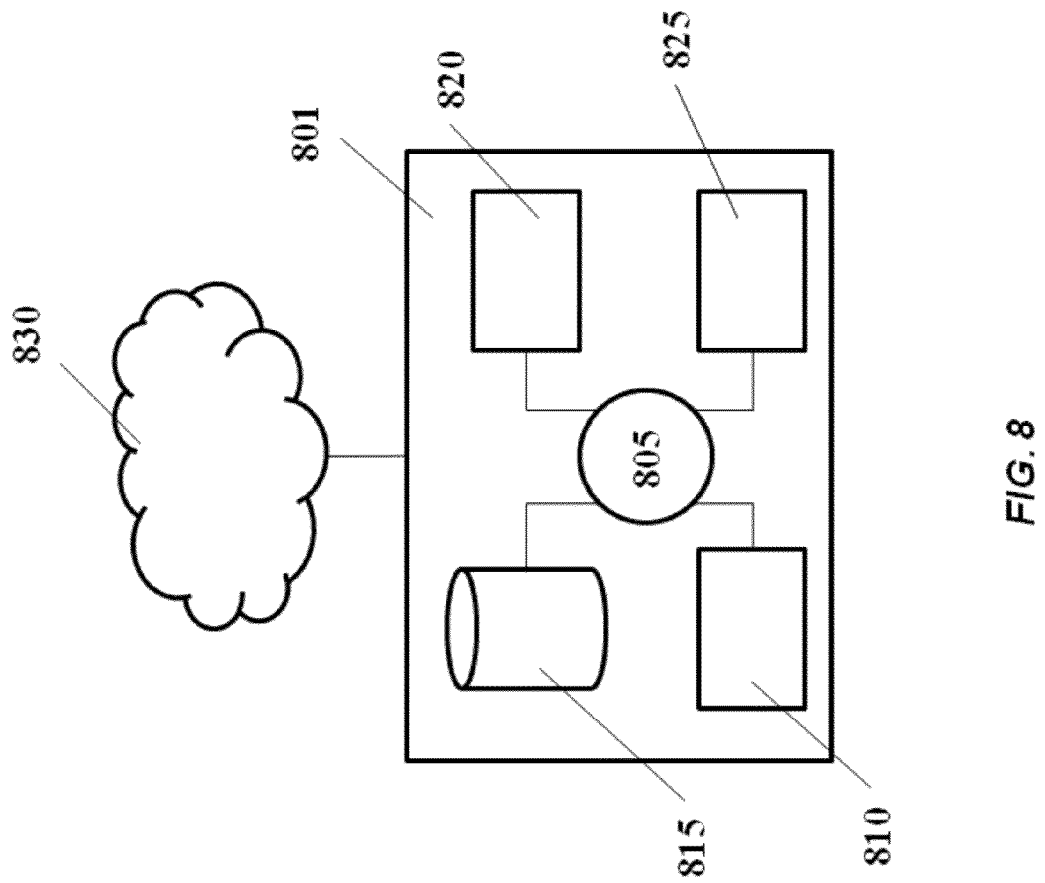
FIG. 8 shows a computer system that is programmed or otherwise configured to implement methods of the present disclosure.

FIG. 8 shows a computer system 801 that is programmed or otherwise configured to regulate droplet formation, droplet heating and skin formation. The computer system 801 can be separate from a droplet generator but in communication with the droplet generator, or be part of the droplet generator, such as integrated with the droplet generator. The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. Examples of operations performed by the CPU 805 can include fetch, decode, execute, and writeback.

The computer system 801 can communicate with one or more remote computer systems through the network 830. For instance, the computer system 801 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Example 1

FIG. 6A shows a system 600 configured for droplet generation. The system 600 includes a controller having electronics (memory, computer processor) for regulating pumps or compressors, which facilitate the flow of fluid in individual droplet generators of a droplet generator cartridge 605 (depicted in FIG. 6B). The controller can also regulate the application of energy to a droplet formed in the droplet generator cartridge 605. The droplet generator cartridge 605 is coupled to the system 600 with the aid of a metal chip support plate 610 on the cartridge 605 and an interface plate 615 in the system 600. The cartridge 605 is removable from the system 600, and can be disposed of after sample processing and analysis (e.g., with the aid of a droplet reader). The metal chip support plate 610 and the interface plate 615 are formed of stainless steel. FIG. 6B is a top view and FIG. 6C is a bottom view of the cartridge 605. The metal chip support plate 610 is shown in FIG. 6C. The droplet generator cartridge 605 includes eight droplet generators, which can have the configuration of FIG. 2. An individual droplet generator 620 is configured to generate droplets in the manner described elsewhere herein. The metal chip support plate 610 is configured to rest against the interface plate 610 of a system 600 for droplet generation.

Figure 7:
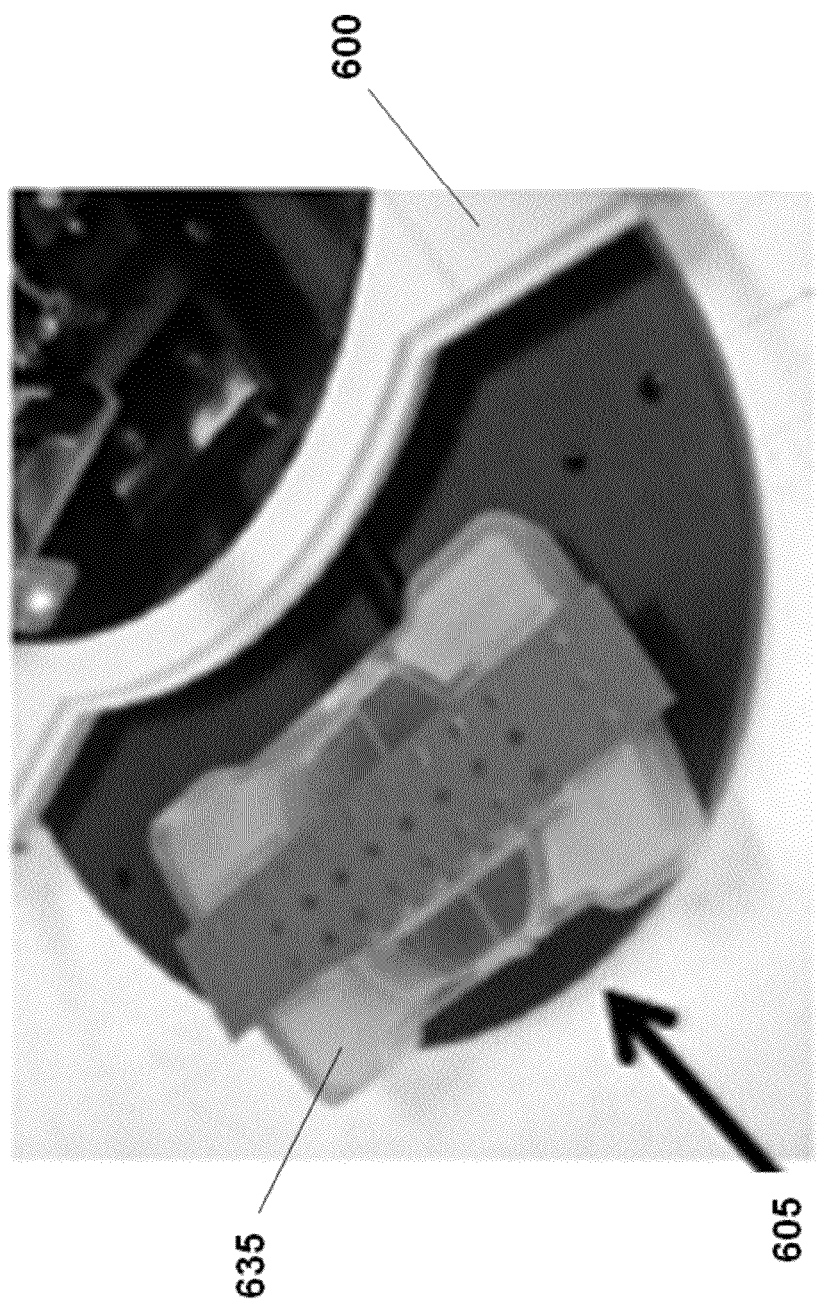
FIG. 7 shows the droplet generator of FIGS. 6B and 6C mounted on the system of FIG. 6A, and a heating element adjacent to the droplet generator, in accordance with some embodiments.

With reference to FIG. 7, during use, the cartridge 605 is mounted on the system 600 by bringing the metal chip support plate 610 in contact with the interface plate 615. The interface plate 615 includes metallic projections 625 that each fit within a slot 630 in the metal chip support plate 610. A heating element 635 is brought in contact with an exposed surface of the cartridge 605. The heating element 635 generates heat, which is transmitted to a droplet channel of the droplet generator. The heating element 635 provides a plurality of energy application zones. Heat can also alternatively or additionally be applied to the droplet channels via the interface between the support plate 610 and the interface plate 615.

The heating element 635 can be separable from the cartridge 605 or integrated with the cartridge 605. In some cases, the heating element 635 is formed in the cartridge 605.

With the cartridge 605 mounted on the system 600, droplets are formed in the droplet generator by applying pressure to the sample and carrier fluid reservoir and/or drawing a vacuum in a droplet reservoir of each of the droplet generators. During droplet formation at a droplet generation point and/or as a droplet flows along a droplet channel (see FIG. 1), heat is applied from the heating element 635 to a droplet to form a skin around the droplet.

The heating rate in the droplet generators 620 is regulated by a controller that is in electrical communication with the heating element 635. The heating rate can be regulated by selecting a voltage that provides a desired or otherwise predetermined power, i.e., $P=i^2/V$, where 'P' is power, 'i' is electrical current and 'V' is voltage applied to the heating element 635. In some cases, the heating rate in the droplet generators 620 is proportion to the power.

The heating element 635 can be in thermal communication an entire droplet generator 620 or the whole cartridge 605. In some cases, the heating element 635 is precluded and heat to the cartridge and the droplet generators 620 is applied with the aid of a heating element mounted on the system, such as the interface plate 615.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:
1. A method for forming a droplet containing a sample to be detected, comprising:
   a. generating a droplet at an intersection of a first channel and a second channel, said first channel in fluid communication with a carrier fluid reservoir and said second channel in fluid communication with a sample reservoir, wherein said droplet is generated by bringing a carrier fluid from said carrier fluid reservoir in contact with a sample or sample partition from said sample reservoir at said intersection;

b. flowing said droplet along a droplet channel leading from said intersection to a droplet reservoir; and c. heating said droplet such that a skin is formed around the droplet by protein denaturation before the droplet enters the droplet reservoir.

2. The method of claim 1, wherein heating said droplet includes a step of applying thermal energy to said droplet with an energy application member as the droplet moves along said droplet channel to said droplet reservoir.

3. The method of claim 1, wherein said droplet flows along said droplet channel as an emulsion.

4. The method of claim 1, wherein said droplet flows along said droplet channel with the aid of a pressure source.

5. The method of claim 1, wherein heating said droplet comprises heating said droplet in said droplet channel.

6. The method of claim 1, wherein heating said droplet stabilizes said droplet.

7. The method of claim 6, wherein heating said droplet prevents said droplet from coalescing with another droplet.

8. The method of claim 1, wherein (a) further comprises generating a plurality of droplets at said intersection.

9. A method for forming a droplet containing a sample or sample partition, comprising:

a. generating a droplet at an intersection of a first channel and a second channel, said first channel in fluid communication with a carrier fluid reservoir and said second channel in fluid communication with a sample reservoir, wherein said droplet is generated by bringing a carrier fluid from said carrier fluid reservoir in contact with a sample partition from said sample reservoir at said intersection;

b. flowing said droplet along a droplet channel leading from said intersection to a droplet reservoir; and c. heating at least a portion of at least one of the channels such that a skin forms around said droplet by protein denaturation.

10. The method of claim 9, wherein said skin stabilizes the droplet.

11. The method of claim 9, wherein said skin prevents said droplet from coalescing with another droplet.

12. The method of claim 9, wherein (a) further comprises generating a plurality of droplets at said intersection.

13. The method of claim 9, wherein heating at least a portion of at least one of the channels includes a step of heating at least a portion of the droplet channel.

\* \* \* \* \*